(12) United States Patent  
Aben

(10) Patent No.: US 12,268,545 B2
(45) Date of Patent: Apr. 8, 2025

(54) METHOD AND SYSTEM FOR CHARACTERIZING VALVULAR REGURGITATION/INSUFFICIENCY FROM SEQUENCES OF IMAGES

(71) Applicant: Pie Medical Imaging B.V., Maastricht (NL)

(72) Inventor: Jean-Paul Aben, Limbricht (NL)

(73) Assignee: Pie Medical Imaging B.V., Maastricht (NL)

(*) Notice: Subject to any disclaimer, the term of this patent is extended or adjusted under 35 U.S.C. 154(b) by 141 days.

(21) Appl. No.: 17/506,180

(22) Filed: Oct. 20, 2021

(65) Prior Publication Data

US 2022/0125398 A1 Apr. 28, 2022

Related U.S. Application Data

(60) Provisional application No. 63/104,320, filed on Oct. 22, 2020.

(51) Int. Cl.
*A61B 6/00* (2024.01)
*A61B 6/50* (2024.01)
(Continued)

(52) U.S. Cl.
CPC ............ *A61B 6/5217* (2013.01); *A61B 6/481* (2013.01); *A61B 6/503* (2013.01); *A61B 6/504* (2013.01);
(Continued)

(58) Field of Classification Search
CPC ....... A61B 6/5217; A61B 6/481; A61B 6/503; A61B 6/504; A61B 6/507; A61B 6/5288;
(Continued)

(56) References Cited

U.S. PATENT DOCUMENTS

| 9,008,386 B2 | 4/2015 | Verstraeten et al. |
| 9,576,360 B2 | 2/2017 | Schormans et al. |
| 2015/0262358 A1* | 9/2015 | Schormans ........... G06T 7/0016 382/103 |

OTHER PUBLICATIONS

Lembcke et al. "Quantification of Functional Mitral Valve Regurgitation in Patients With Congestive Heart Failure", 2004, Investigative Radiology, vol. 39, No. 12, p. 728-739 (Year: 2004).*

(Continued)

*Primary Examiner* — Colin T. Sakamoto
*Assistant Examiner* — Andrew W Begeman
(74) *Attorney, Agent, or Firm* — Gordon & Jacobson, P.C.

(57) ABSTRACT

Method and systems are provided for characterizing blood flow in an atrioventricular valve of the human heart, the atrioventricular valve connecting an atrium with a corresponding ventricle of the heart, the ventricle being fluidly coupled to a particular vessel that transports blood outside the ventricle blood, which involve obtaining image data of the heart and identifying contours of the atrium and a region within the particular vessel within the image data. A time-density curve for the atrium can be calculated from the contour of the atrium and densitometric image data derived from the image data. A time-density curve for the region of the particular vessel can be calculated from the contour of the vessel region and the densitometric image data. Data that characterizes at least one regurgitation fraction related to the atrioventricular valve can be calculated from such time-density curves.

22 Claims, 17 Drawing Sheets

(51) Int. Cl.
| | |
|---|---|
| G06T 7/246 | (2017.01) |
| G06T 7/62 | (2017.01) |
| G06V 10/44 | (2022.01) |
| G16H 30/40 | (2018.01) |
| G16H 50/30 | (2018.01) |

(52) U.S. Cl.
CPC ............ *A61B 6/507* (2013.01); *A61B 6/5288* (2013.01); *G06T 7/248* (2017.01); *G06T 7/62* (2017.01); *G06V 10/44* (2022.01); *G16H 30/40* (2018.01); *G16H 50/30* (2018.01); *A61B 6/487* (2013.01); *G06T 2207/10116* (2013.01); *G06T 2207/10121* (2013.01); *G06V 2201/031* (2022.01)

(58) Field of Classification Search
CPC . G06T 7/248; G06T 7/62; G06T 2207/10116; G06V 10/44; G06V 2201/031; G16H 30/40; G16H 50/30
See application file for complete search history.

(56) References Cited

OTHER PUBLICATIONS

Murata et al. "Time-course of left atrial performance during coronary artery occlusion followed by reperfusion in anesthetized dogs by densitometric analysis of digital atrioventriculographic images", 1993, Basic Research in Cardiology, vol. 88, p. 259-271 (Year: 1993).*
Kozerke et al., "Aortic and Mitral Regurgitation: Quantification Using Moving Slice Velocity Mapping", Journal of Magnetic Resonance Imaging, vol. 14, p. 106-112 (Year: 2001).*
Pettigrew et al., "MRI Techniques for Cardiovascular imaging", 1999, Journal of Magnetic Resonance Imaging, vol. 10, p. 590-601 (Year: 1999).*
Lembcke et al., "Changes in Right Ventricular Dimensions and Performance After Passive Cardiac Containment", 2004, the society of Thoracic Surgeons, vol. 78, p. 900-905 (Year: 2004).*
Cardozo et al., "Is bacteriostatic saline superior to normal saline as an echocardiographic contrast agent?", 2014, Int J Cardiovasc Imaging, vol. 30, p. 1483-1489 (Year: 2014).*
Seemann et al., "Valvular Imaging in the Era of FeatureTracking: A Slice-Following Cardiac MR Sequence to Measure Mitral Flow", 2019, Journal of Magnetic resonance imaging, vol. 51, p. 1412-1421 (Year: 2019).*
Wikipedia, "Electron beam computed tomography", 2019 (Year: 2019).*
"A Real-Time QRS Detection Algorithm", Pan et al., IEEE Transactions on Biomedical Engineering. BME-32 (3): 230-236.
"A Registration-Based Propagation Framework for Automatic Whole Heart Segmentation of Cardiac MRI", Zhuang et al, IEEE Transaction on Medical Imaging Sep. 2010;29(9):1612-25.
"Asymptomatic aortic stenosis in the elderly: a clinical review", Manning et al., 2013 JAMA, 310(14), 1490-1497.
"Determination of left ventricular volumes by Simpson's rule in infants and children with congenital heart disease", Ino et al., British Heart Journal Feb. 1989; 61(2):182-185.
"Left retrograde cardioangiography in acquired cardiac disease: Technic, indications and interpretations in 700 cases", Sellers RD et al., Am J Cardiol. 1964;14:437-447.
"Non-rigid image registration: theory and practice", Crum et al, The British Journal of Radiology; 77 (2004), S140-S153.
"Outcome of 622 adults with asymptomatic, hemodynamically significant aortic stenosis during prolonged follow-up", Pellikka et al., 2005 Circulation, 111(24), 3290-3295.
"Quantitative Assessment of Acute Regurgitation Following TAVR: A Multicenter Pooled Analysis of 2,258 Valves", Modolo et al., JACC Cardiovasc Interv 2020;13:1303-1311.
"Right ventricular volume determinations in children, normal values and observations with volume or pressure overload", Graham TP et al., Circulation; Jan. 1973, pp. 144-153.
"Video densitometric assessment of aortic regurgitation after transcatheter aortic valve implantation: results from the Brazilian TAVI registry", Tateishi et al., EuroIntervention 2016; 11:1409-18.
"Videodensitometric quantification of paravalvular regurgitation of a transcatheter aortic valve: in vitro validation", Abdelghani et al., EuroIntervention 2018;13:1527-1535.
EP Search Report dated Mar. 11, 2022 of application No. EP21203957.
"Gated radionuclide angiographic evaluation of valve regurgitation", Bough E W et al, American Journal of Cardiology, Cahners Publishing Co., Newton, MA, US, vol. 46, No. 3, doi: 10.1016/0002-9149(80)90011-9, ISSN 0002-9149, (Sep. 1, 1980), pp. 423-428, (Sep. 1, 1980), XP023197649; 1980.
"Quantitation of valvular insufficiency by computerized radionuclide angiocardiography", Kirch D L et al, American Journal of Cardiology, Cahners Publishing Co., Newton, MA, US, vol. 34, No. 6, doi: 10.1016/0002-9149(74)90162-3, ISSN 0002-9149, (Nov. 1, 1974), pp. 711-721, (19741101), XP026334191.
"Standardized image interpretation and post processing in cardiovascular magnetic resonance: Society for Cardiovascular Magnetic Resonance (SCMR) Board of Trustees Task Force on Standardized Post Processing", Jeanette Schulz-Menger et al, Journal of Cardiovascular Magnetic Resonance, Biomed Central Ltd, London UK, (May 1, 2013), vol. 15, No. 1, doi: 10.1186/1532-429X-15-35, ISSN 1532-429X, p. 35, XP021153423.

* cited by examiner

METHOD AND SYSTEM FOR CHARACTERIZING VALVULAR REGURGITATION/INSUFFICIENCY FROM SEQUENCES OF IMAGES

CROSS-REFERENCE TO RELATED APPLICATION(S)

The present application claims priority from U.S. Prov. Appl. No. 63/104,320 entitled "METHOD AND SYSTEM FOR CHARACTERIZING VALVULAR REGURGITATION/INSUFFICIENCY FROM SEQUENCES OF IMAGES," filed on Oct. 22, 2020, herein incorporated by reference in its entirety.

BACKGROUND

1. Field

The present application relates to the technical field of medical imaging, particularly angiography imaging, although it can find application in any field where there is the need to quantify regurgitation or insufficiency of any valve closing the outlet of a moving organ such as in non-destructive testing applications.

2. State of the Art

Valvular regurgitation (also known as valvular insufficiency) is a cardiac disease characterized by the failure of the cardiac valves to close perfectly, resulting in blood flowing in the opposite direction and thereby causing regurgitation or leakage. Such valvular regurgitation/inefficiency can be experienced by one or more of the four cardiac valves; aortic valve, mitral valve, pulmonary valve, and the tricuspid valve. Valvular insufficiency/regurgitation represent the dominant functional and anatomic consequences associated with valvular heart disease, due to the higher workload and a higher pressure within the heart, increasing the chances of heart failure. Patients may experience chest pains, become quickly out of breath if they exert themselves and may suffer fainting spells as well as other symptoms. Eventually, they develop more serious complications including heart failure. There is no medication that can reverse the damage. There are several methods available to assess valvular regurgitation, such as electrocardiogram (ECG), transthoracic echocardiography (TTE), transesophageal echocardiography (TEE), magnetic resonance imaging (MRI).

Surgical valve replacement or valve repair is the standard of care in patients with severe valvular regurgitation. Surgical valve replacements/repair involves open heart surgery in which the surgeon repairs or replaces (by a mechanical or tissue valve) the patient's diseased valve. The patient is placed on a heart-lung bypass machine while the heart is stopped.

Not all patients can withstand the risks associated with surgical valve repair or replacement. Roughly one-third of all patients with severe aortic stenosis are considered too high risk for open-heart surgery (Manning et al., "Asymptomatic aortic stenosis in the elderly: a clinical review", 2013 JAMA, 310(14), 1490-1497). About 50% of this group of patients die within one to two years without corrective therapies (Pellikka et al., "Outcome of 622 adults with asymptomatic, hemodynamically significant aortic stenosis during prolonged follow-up", 2005 Circulation, 111(24), 3290-3295).

Recently, transcatheter valve replacement and transcatheter valve repair (TVR) has been developed as an alternative to the open-heart surgical approach. TVR involves a minimally invasive procedure which repairs or replaced the valve without removing the old, damaged valve. Instead, it wedges a replacement valve or repair device towards the diseased valve's place. The repair or replacement device is delivered through one of several access methods: transfemoral (in the upper leg), transapical (through the wall of the heart), subclavian (beneath the collar bone), or transcaval (from a temporary hole in the aorta near the belly button through a vein in the upper leg). As an added bonus, the recovery time is much faster for TVR patients who are typically out of hospital within three to five days. Open-heart surgery patients spend about 10 days in hospital and it takes a long time for their chest incision to heal.

TVR is performed minimally invasively during a catheterization procedure with the guidance of X-ray angiography and precise assessment of valvular regurgitation (VR) severity is needed during procedure when there is still a chance to avert it. Quantification of VR, typically and most commonly paravalvular, is challenging and frequently requires a multimodality assessment. TEE and x-ray angiography are the standard tools for the assessment of VR during the procedure. However, echocardiography has a low reproducibility and a low sensitivity to detect paravalvular leaks, and the Sellers' method (Sellers R D et al., "Left retrograde cardioangiography in acquired cardiac disease: Technic, indications and interpretations in 700 cases", Am J Cardiol. 1964;14:437-447) of x-ray angiography assessment is qualitative and subjective.

Within U.S. Pat. No. 9,576,360 a novel videodensitometric approach was introduced for the accurate assessment of aortic (para)valvular regurgitation during a transcatheter aortic valve implantation. This method has been extensively validated and proven to be very robust and reproducible by several authors; Abdelghani et al., "Videodensitometric quantification of paravalvular regurgitation of a transcatheter aortic valve: in vitro validation", EuroIntervention 2018;13:1527-1535, Modolo et al., "Quantitative Assessment of Acute Regurgitation Following TAVR: A Multicenter Pooled Analysis of 2,258 Valves", JACC Cardiovasc Intery 2020;13:1303-1311, and by Tateishi et al., "Video densitometric assessment of aortic regurgitation after transcatheter aortic valve implantation: results from the Brazilian TAVI registry", EuroIntervention 2016;11:1409-18.

The method described by U.S. Pat. No. 9,576,360 is focused on the quantitative assessment of the aortic valve, which can be considered as a two-compartment problem. However, quantification of (para)valvular regurgitation of the mitral valve or the tricuspid valve, which can be considered as a three-compartment problem, is not addressed.

Assessment of (para)valvular regurgitation for the atrioventricular valves (i.e., the mitral valve or tricuspid valve) using the method as described by U.S. Pat. No. 9,576,360 is error prone. Due to the relatively large region of the ventricle (the reference region), it is not likely to obtain homogeneous contrast filling, which hampers time-density curve assessment. Moreover, the contrast density within the ventricle will be variable by nature, this due to the change in ventricle shape and volume as a result of the cardiac cycle. Moreover, if both the atrioventricular valve and the ventricular valve suffer from (para)valvular regurgitation a two-compartment method is not sufficient.

There is thus the need to improve the assessment of valvular regurgitation such as mitral and tricuspid regurgitation by computer analysis using x-ray angiography image data.

SUMMARY

The present application describes methods and systems for characterization of valvular regurgitation based on image data, such as a two-dimensional (2D) angiographic film of X-ray image. Image data of the heart is acquired by an imaging system and stored in electronic form or otherwise obtained. Such image data can be analyzed to identify a contour of at least one vascular object of interest within the image data. The image data converted to densitometric image data. A time-density curve for the least one vascular object of interest is calculated from the contour of the at least one vascular object of interest and the densitometric image data. Data that characterizes regurgitant flow in at least one valve of the heart is generated from the time-density curve.

In embodiments, the data generated from the time-density curve quantifies regurgitant flow in at least one valve of the heart selected from the group consisting of: mitral valve, aortic valve, tricuspid valve, and pulmonary valve.

In embodiments, the image data can be analyzed to identify contours for a plurality of vascular objects of interest. A plurality of time-density curves can be calculated for the plurality of vascular object of interests from such contours and the densitometric image data. The data that characterizes regurgitant flow in at least one valve of the heart can be generated from the plurality of time-density curves.

In embodiments, the densitometric image data comprises pixel values that represent localized density of absorbed radiation due to contrast liquid over time.

In embodiments, the time-density curve represents localized density of absorbed radiation due to contrast agent by a vascular object of interest over time.

In embodiments, the image data covers a first period of time prior to injection of contrast agent into the heart and a second period of time after injection of contrast agent into the heart.

In embodiments, the contour of the at least one vascular object of interest can be identified in a particular image frame.

In embodiments, the contour of the at least one vascular object of interest can be identified by user input and/or automatic processes.

In embodiments, the image data can be angiographic x-ray image frames.

In embodiment, at least some (or all) of the operations of the method and system can be performed by a processor.

In embodiments, the methods and systems can characterize blood flow in an atrioventricular valve of the human heart, where the atrioventricular valve connects an atrium with a corresponding ventricle of the heart, and the ventricle is fluidly coupled to a particular vessel that transports blood outside the ventricle. Specifically, the methods and systems can identify a contour of the atrium within image data of the heart, and can identify a contour of a region within the particular vessel within the image data. A time-density curve for the atrium can be calculated from the contour of the atrium and the densitometric image data. A time-density curve for the region of the particular vessel can be calculated from the contour of the vessel region and the densitometric image data. Data that characterizes at least one regurgitation fraction related to valvular regurgitation of the heart can be generated from such time-density curves.

In embodiments, the methods and systems can involve calculating data representing forward blood flow from the ventricle to the particular vessel from the time density curve for the vessel region based on area under such time-density curve starting from a contrast arrival frame over a number of cardiac cycles. The methods and systems can also involve calculating data representing regurgitant blood flow from the ventricle to the atrium from the time density curve of the atrium based on area under such time-density curve starting from the contrast arrival frame over the number of cardiac cycles.

In embodiments, the methods and systems can involve calculating a first regurgitant fraction from the data representing forward blood flow from the ventricle to the particular vessel and the data representing regurgitant blood flow from the ventricle to the atrium. For example, the first regurgitant fraction can be calculated as $$\frac{AtrioventricularValve_{backward\ flow}}{VentriculaValve_{forward\ flow} + AtrioventrocularValve_{backward\ flow}},$$

wherein VentriculaValve$_{forward\ flow}$ comprises the data representing forward blood flow from the ventricle to the particular vessel, and AtrioventricularValve$_{backward\ flow}$ comprises the data representing regurgitant blood flow from the ventricle to the atrium.

In embodiments, the methods and systems can involve calculating data representing regurgitant blood flow from the particular vessel to the ventricle from the time density curve for the vessel region.

In embodiments, the methods and systems can involve calculating data representing regurgitant blood flow from the particular vessel to the ventricle based on area under the time density curve for the vessel region within the diastolic phase of the heart after the contrast arrival frame.

In embodiments, the methods and systems can involve calculating a second regurgitant fraction from the data representing regurgitant blood flow from the particular vessel to the ventricle. For example, the second regurgitant fraction can be calculated as $$\frac{AtrioventricularValve_{backward\ flow}}{VentricularValve_{forward\ flow} - VentricularValve_{backward\ flow} + AtrioventrocularValve_{backward\ flow}},$$

wherein VentriculaValve$_{forward\ flow}$ comprises data representing forward blood flow from the ventricle to the particular vessel, AtrioventricularValve$_{backward\ flow}$ comprises data representing regurgitant blood flow from the ventricle to the atrium, and VentricularValve$_{backward\ flow}$ comprises the data representing regurgitant blood flow from the particular vessel to the ventricle.

In embodiments, the methods and systems can involve identifying the ventricle of the heart within the image data for at least two moments within the cardiac cycle, and calculating a stroke volume based on ventricular volume at the diastolic phase of the heart and ventricular volume at the systolic phase of the heart. Data that characterizes regurgitant flow in at least one atrioventricular valve of the heart can be calculated from the at least one regurgitation fraction and the stroke volume.

In embodiments, the contours can correspond to the left atrium of the heart and a region of the ascending aorta of the heart, and the data generated from the corresponding time density curves can characterize regurgitation fractions for both the mitral valve and the aortic valve of the heart.

In other embodiments, the contours can correspond to the right atrium of the heart and a region of the pulmonary artery of the heart, and the data generated from the corresponding time density curves can characterize regurgitation fractions for both the tricuspid valve and the pulmonary valve of the heart.

In embodiments, the methods and systems can generate the data that characterizes the at least one regurgitation fraction based on conservation of mass of forward and backward flows related to an atrioventricular valve of the heart.

In embodiments, the time density curves can be normalized relative to a selected time density curve.

In embodiments, the data characterizes at least one regurgitation fraction can be based on difference between particular time density curves relative to a predefined phase of the heart cycle.

BRIEF DESCRIPTION OF THE DRAWINGS

The characteristics of the invention and the advantages derived therefrom will be more apparent from the following description of non-limiting embodiments, illustrated in the annexed drawings, in which.

DETAILED DESCRIPTION

The present application relates to methods and systems for characterization of valvular regurgitation/insufficient based on sequences of images, such as two-dimensional (2D) angiographic film of X-ray images. It will be mainly disclosed with reference to this field. Within current application the term image or image frame refers to a single image and the term image sequence refers to a multiple images acquired over time and when used in relation to x-ray it comprises multiple frames covering one or more phases of the cardiac cycle.

Figure 1:
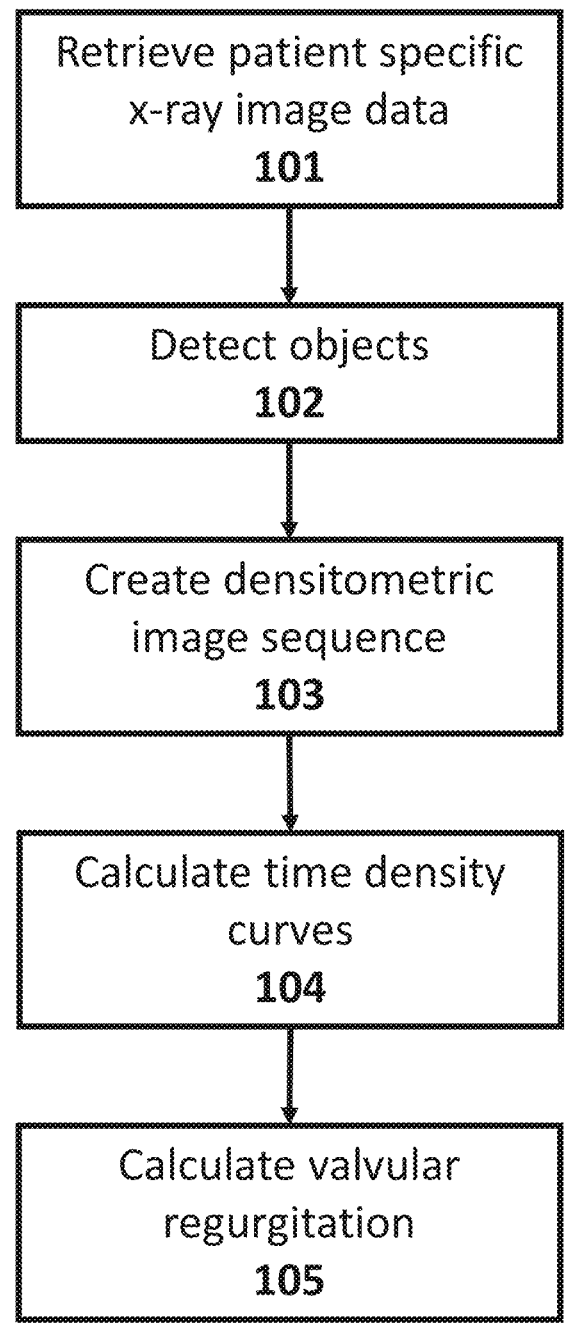
FIG. 1 shows a flow chart of a method for determining valvular regurgitation in accordance with an embodiment herein.

FIG. 1 shows a flow chart illustrating the operations according to an embodiment of the present application. The operations employ an imaging system capable of acquiring and processing two-dimensional image sequences of a vessel organ (or portion thereof) or other object of interest. For example, a single plane or bi-plane angiographic system can be used such to acquire the X-ray image data as those manufactured, for example, by Siemens (Artis zee Biplane) or Philips (Allura Xper FD).

Figure 2:
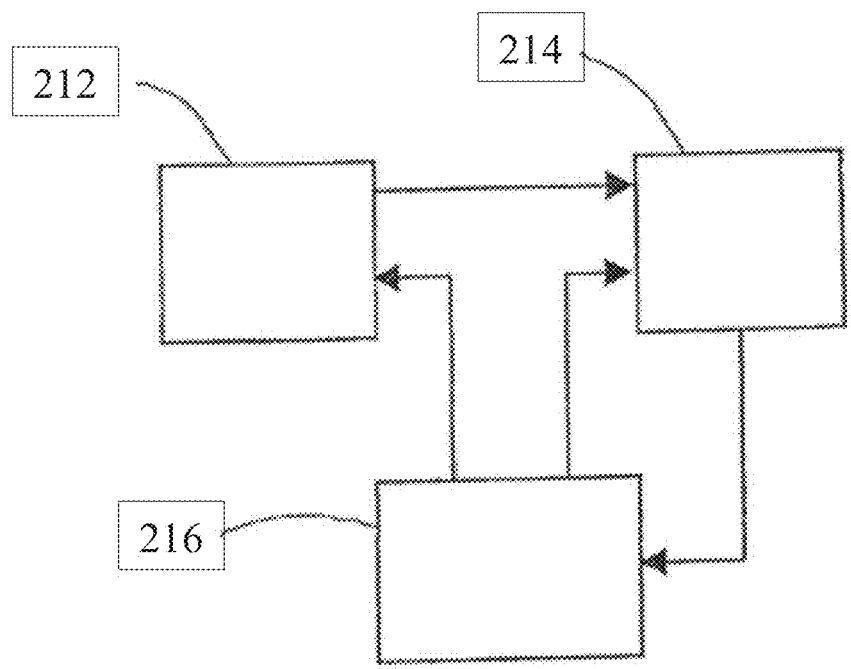
FIG. 2 shows a functional block diagram of an exemplary single plane angiographic system.

FIG. 2 is a functional block diagram of an exemplary single plane angiographic system, which includes an angiographic imaging apparatus 212 that operates under commands from user interface module 216 and will provide data to data processing module 214. The single plane angiographic imaging apparatus 212 captures a two-dimensional X-ray image sequence of the vessel organ of interest, for example, in the postero-anterior direction. The single plane angiographic imaging apparatus 212 typically includes an X-ray source and detector pair mounted on an arm of a supporting gantry. The gantry provides for positioning the arm of the X-ray source and detector at various angles with respect to a patient who is supported on a table between the X-ray source and detector. The data processing module 214 may be realized by a personal computer, workstation, or other computer processing system. The data processing module 214 processes the two-dimensional image sequence captured by the single plane angiographic imaging apparatus 212 to generate data as described herein. The user interface module 216 interacts with the user and communicates with the data processing module 214. The user interface module 216 can include different kinds of input and output devices, such as a display screen for visual output, a touch screen for touch input, a mouse pointer or other pointing device for input, a microphone for speech input, a speaker for audio output, a keyboard and/or keypad for input, etc. The data processing module 214 and the user interface module 216 cooperate to carry out the operations of FIG. 1 as described below.

The operations of FIG. 1 can also be carried out by software code that is embodied in a computer product (for example, an optical disc or other form of persistent memory such as a USB drive or a network server). The software code can be directly loadable into the memory of a data processing system for carrying out the operations of FIG. 1. Such data processing system can also be physically separated from the angiographic system used for acquiring the images making use of any type of data communication for getting such images as input.

In this example it is assumed that the x-ray imaging system has acquired and stored at least one two-dimensional image sequence of the vessel organ of interest (e.g., human heart or portions thereof). Any image device capable of providing two-dimensional angiographic image sequences can be used for this purpose. For example, a bi-plane or single plane angiographic system can be used such as those manufactured, for example, by Siemens (Artis zee Biplane) or Philips (Allura Xper FD).

An embodiment is now disclosed with reference to FIG. 1. The therein-depicted operations can, obviously, be performed in any logical sequence and can be omitted in parts. As it is an objective of the application to provide a select (e.g. optimal) workflow that can be used during the interventions, workflow example steps will also be referenced.

Figure 3A:
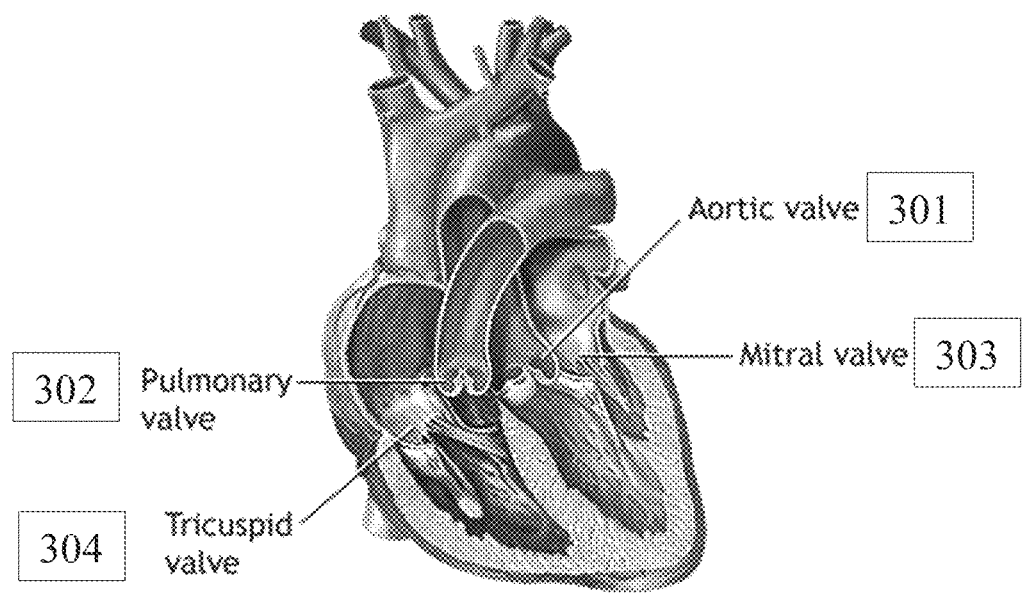
FIG. 3A shows the anatomy of the heart with focus on the four cardiac valves.
Figure 3B:
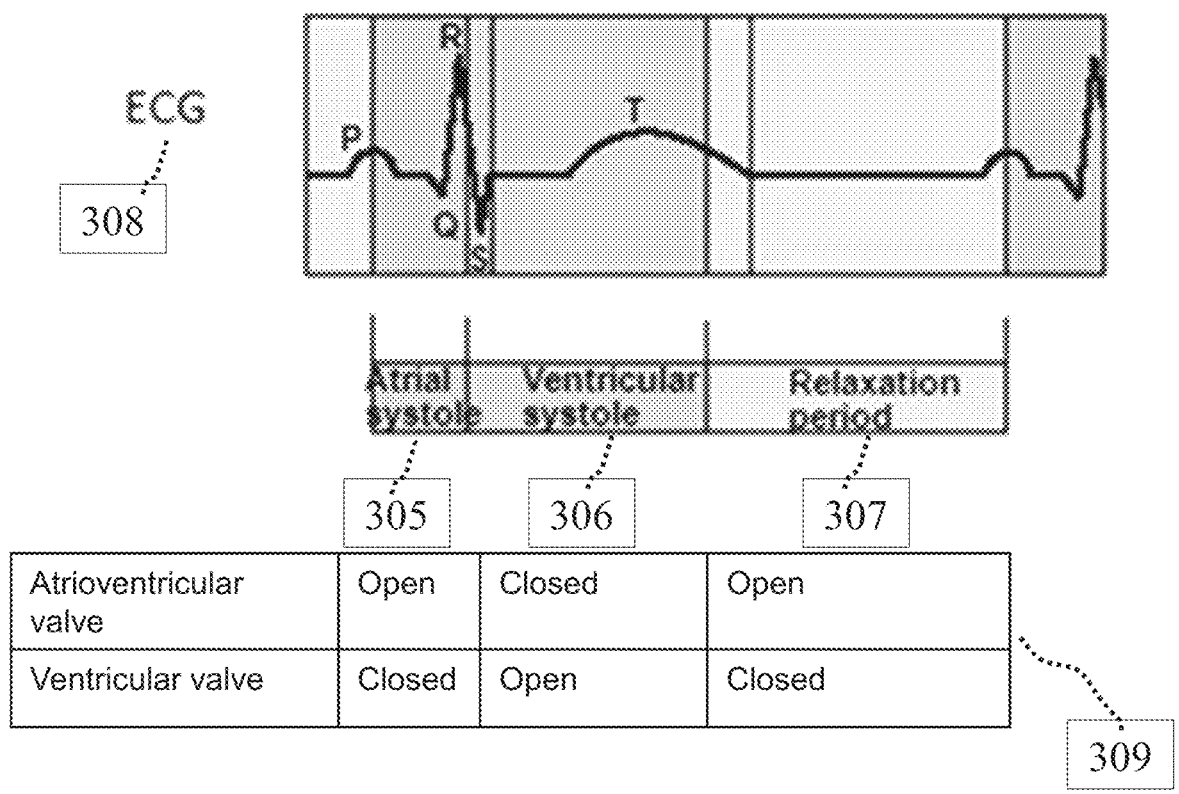
FIG. 3B illustrates the three main states of the heart and the relation with opening and closing of the valves.

Frist an overview of the different heart valves and how they behave in the different heart states is described. The human heart has four valves as shown in FIG. 3A. There are two ventricular valves; the aortic valve (301) and the pulmonary valve (302), and two atrioventricular valves; the mitral valve (203) and tricuspid valve (204). During a cardiac cycle as shown in FIG. 3B, three main states of the heart can be identified, which are: arterial systole (305), ventricular systole (306) and relaxation period (307). FIG. 3B shows the different heart states with respect to the ECG signal (308) as well as an overview on the status of the valves by table 309. During the arterial systole (305), the atrial valves (mitral, tricuspid) are open, and the ventricular valve (aorta, pulmonary) are closed. Blood flows from the atrial chambers in the ventricular chambers. During ventricular systole (306) the ventricles contracts and the ventricular valves are open, and the atrial valves are closed. Blood is pumped from the ventricular chambers to the lungs (through the pulmonary artery) and to the organs of the body (though the aortic artery). During the relaxation period (307), the ventricular valves are closed, and the atrial valves are open. Blood flows from the major veins (pulmonary veins and vena cava) into the atria's and from there into the ventricles. The cardiac cycle is can also be identified as two phases; systole phase and diastole phase. Systole phase includes the ventricular systole, as diastole phase includes arterial systole and relaxation period.

As can be seen in FIG. 1, the workflow comprises of number of steps or operations, and the workflow will be described to detect and characterize valvular regurgitation (also called valvular insufficiency) of the valves of the heart (for the left side of the heart these are the mitral valve and aortic valve). Such valvular regurgitation is a condition in which the heart's valve does not close tightly, allowing blood to leak or flow through the valve during the period of the cardiac cycle that is should be closed tightly. If such valvular regurgitation is significant, blood movement through the patient's heart and to the rest of the patient's body is inefficient and can make the patient feel tired or out of breath. The disclosed method is not limited to the left side of the heart and can also be performed for the right side of the heart, for the tricuspid valve and pulmonary valve. For this, the patient specific x-ray image data should visualize the right chamber(s) of the heart.

Figure 4:
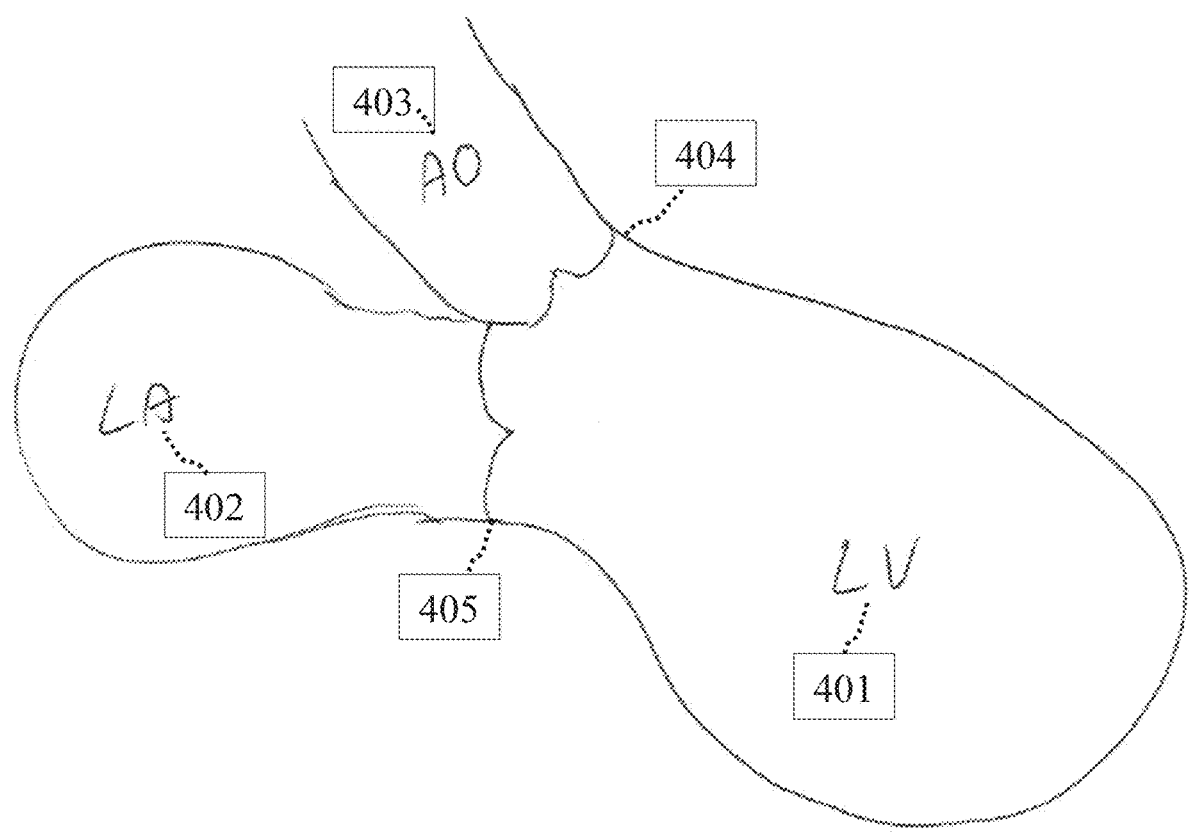
FIG. 4 shows the three compartments of the left side of the heart important to assess mitral regurgitation.

The first step (101) of FIG. 1 involves the retrieval of the patient specific x-ray image data which consists of a sequence of angiographic x-ray image frames covering approximately one heart cycle before the injection of the contrast liquid and approximately three heart cycles after the injection of the contrast liquid. To assess mitral regurgitation, the contrast is injected into the left chamber of the heart (left ventricle), and a projection is chosen which shows the three compartments; left ventricle (LV) 401, left atrium (LA) 402, and ascending aorta (AO) 403, with a minimum of overlap to each other as shown by FIG. 4. Also illustrated by FIG. 4, the aortic valve (404) which separates the LV from the AO, and the mitral valve (405) which separates the LV from the LA. Furthermore, care should be taken to avoid overlay of the descending aorta with the LA. An x-ray projection which fulfills above could be achieved by for instance a rotation of approximately RA055 degrees and an angulation of approximately CAU30 degrees and might be depended on the specific patient anatomy.

Figure 5:
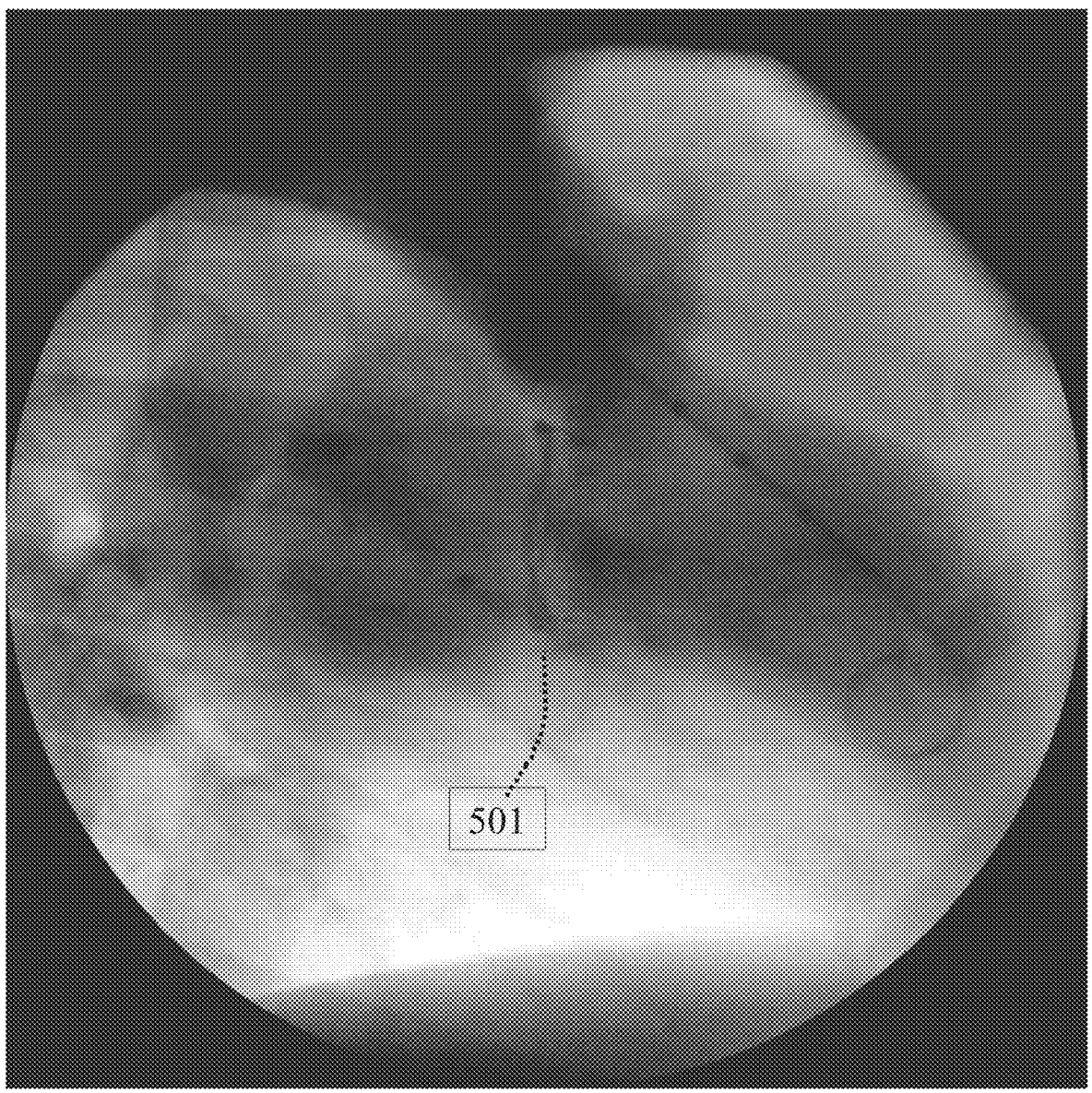
FIG. 5 shows an example of a single frame within an acquired x-ray angiographic image sequence in which a replaced mitral valve is visible.
Figure 6:
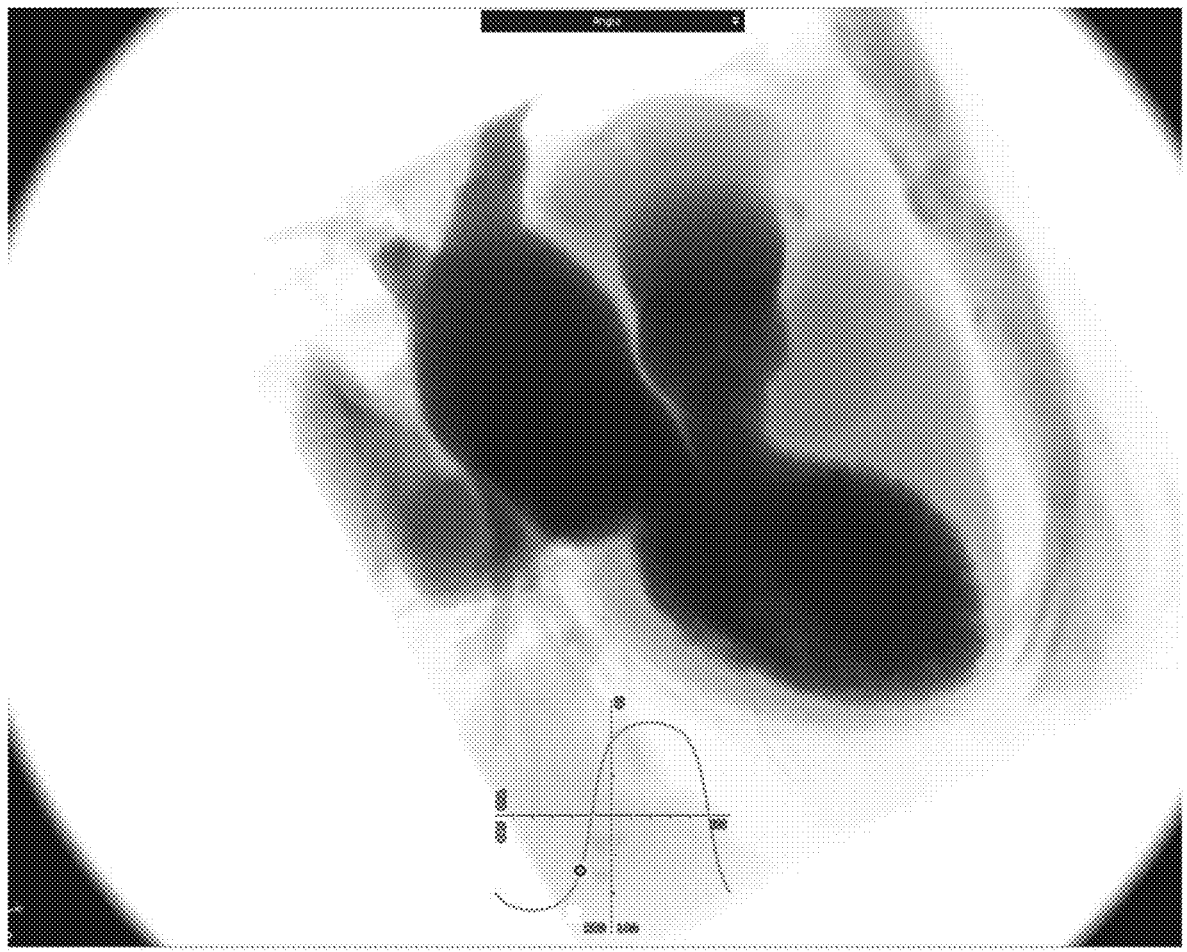
FIG. 6 provides an example of obtaining the optimal projection by using the simulated angioview within the 3mensio Structural Heart software.

FIG. 5 shows an example of a single frame within an acquired x-ray angiographic image sequence in which a replaced mitral valve (501) is visible. The frame shown is around systolic after injection of the contrast liquid. Alternatively, the patient specific projection can be obtained by means of planning on a pre-procedural three-dimensional (3D) image data sets, for instance computed tomography (CT), such as 3mensio Structural Heart software 10v1 (Pie Medical Imaging, Maastricht, the Netherlands) or Heart Navigator Software (Philips Healthcare, The Netherlands). FIG. 6 provides an example of obtaining the optimal projection by using the simulated angioview (disclosed by U.S. Pat. No. 9,008,386) within the 3mensio Structural Heart software.

Within step 102 of FIG. 1, the contours of two objects of interest, the aorta (or AO) and the left atrium (or LA), are detected to quantify mitral valve regurgitation. Typically, a frame is selected in which the aortic valve is going to be opened but still is closed. Referring to FIG. 3B such a frame, further referred to as optimal frame, corresponds to end of atrial systole state and can be identified based on the ECG signal as available through the "headers" of the Digital Imaging and Communications in Medicine (DICOM) file or by visual assessment of the x-ray angiographic image sequence. Detection of specific features within the ECG signal, in our case the r-tops, can be performed as for example taught by Pan et al., "*A Real-Time QRS Detection Algorithm*", IEEE Transactions on Biomedical Engineering. BME-32 (3): 230-236. The optimal frame(s) can be defined as a percentage between two consecutive r-peaks. This percentage is typically 5%. When incorporating the knowledge at which frame the contrast arrives within the left ventricle, as further explain in step 103, the most optimal frame which is the optimal frame in which the AO is opacified (due to the contrast liquid) can be automatically detected.

Figure 7:
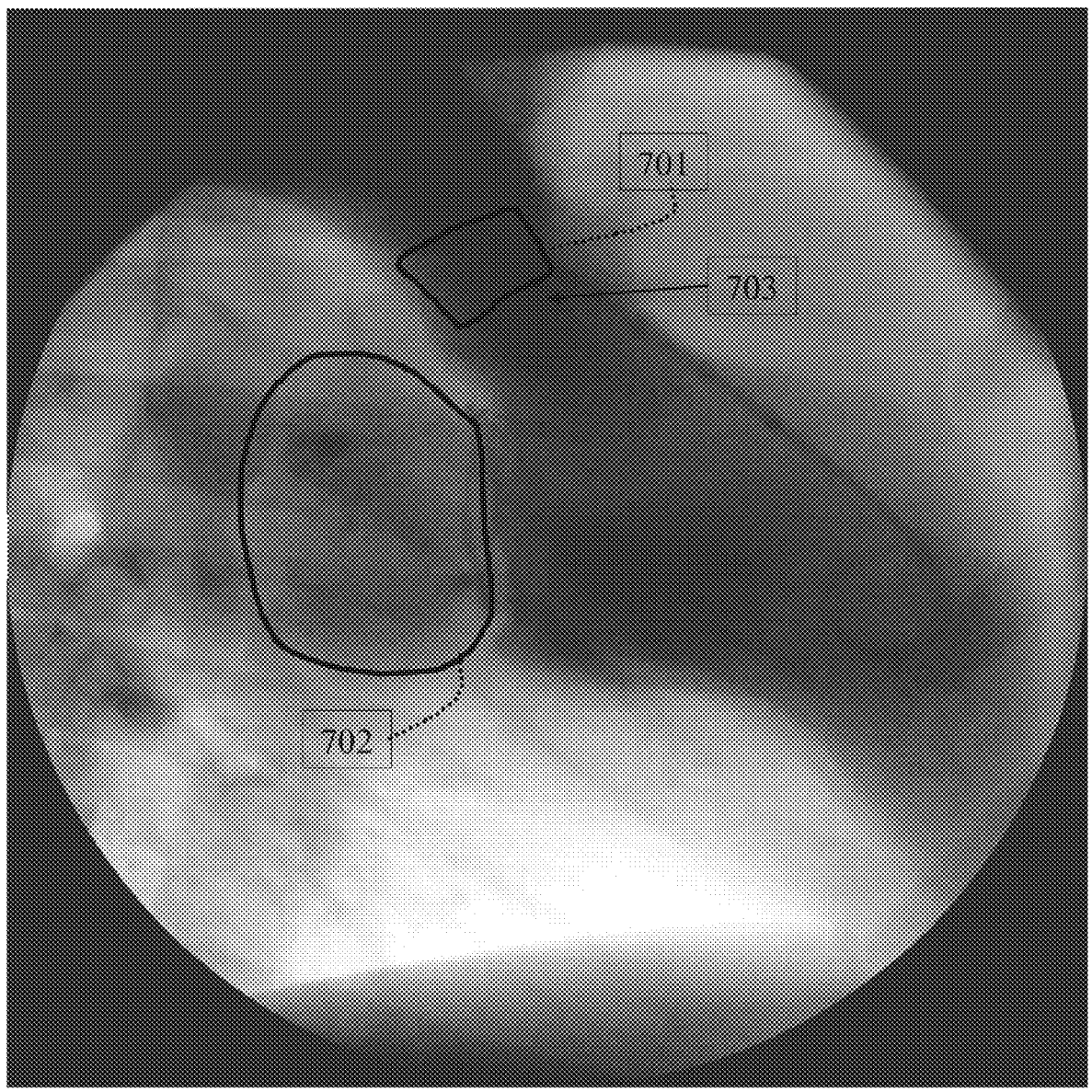
FIG. 7 shows an example of the detection of two objects in the most optimal frame.
Figure 8:
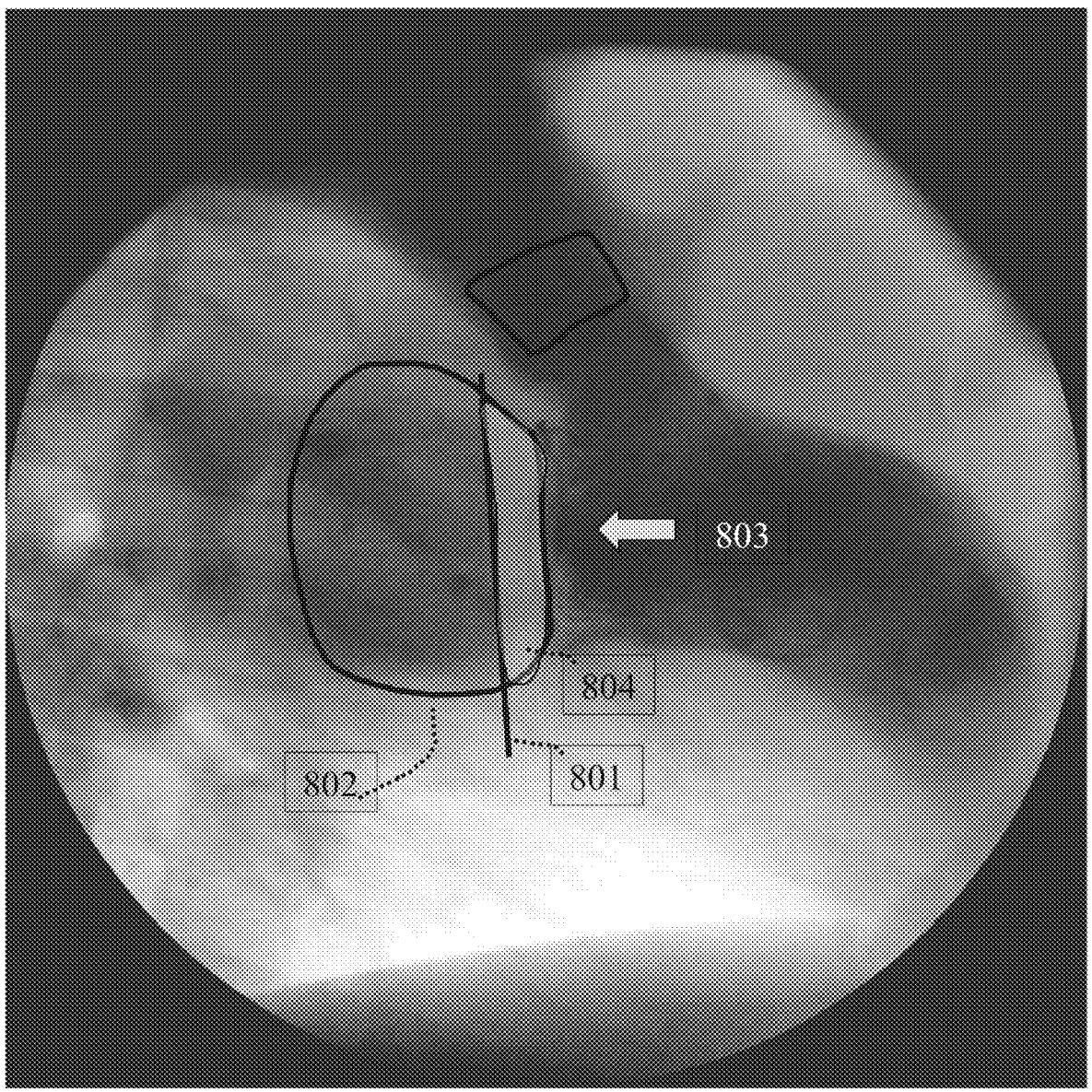
FIG. 8 shows an example a reference line drawn which delimits the left ventricle from the left atrium within the x-ray sequence.

FIG. 7 shows the detection of the two objects in the most optimal frame by means of a manual segmentation. The contour or region of the AO, identified by 701, is manually drawn covering the AO above the aortic valve (703), and the contour or region of the LA, identified by 702, is manually drawn covering the left atrium. In case the selected frame does not represent the end of the atrial systole state, a reference line can be drawn which delimits the left ventricle from the left atrium within the x-ray sequence as illustrated by FIG. 8 (801). In case the selected frame represent the end of the atrial systole state, the motion of the mitral valve, illustrated by the arrow 803, is in the most extreme location in which the contour or region of the LA does not overlap the left ventricle during the cardiac cycle. Within FIG. 8, the region 804 within the contour or region of the segmented LA region (802) will not be taken into consideration for the quantification of the mitral regurgitation as explained by step 105 of FIG. 1. The region 804 represents to the movement of the mitral valve during the cardiac cycle.

Alternatively, the contour of region of the AO and the contour or region of the LA can be superimposed from segmentation performed on the pre-procedural 3D image data sets such as CT by means of the 3mensio Structural Heart software, the Heart Navigator Software, or other pre-procedural planning software. In summary, the regions are segmented using the 3D image data and the resulting 3D segmented regions are then registered to the x-ray angiographic dataset for a selected frame as for instance described by Crum et al, "Non-rigid image registration: theory and practice", The British Journal of Radiology; 77 (2004), S140-S153, or by Zhuang et al, "A Registration-Based Propagation Framework for Automatic Whole Heart Segmentation of Cardiac MRI", IEEE Transaction on Medical Imaging 2010 September;29(9):1612-25.

Figure 16:
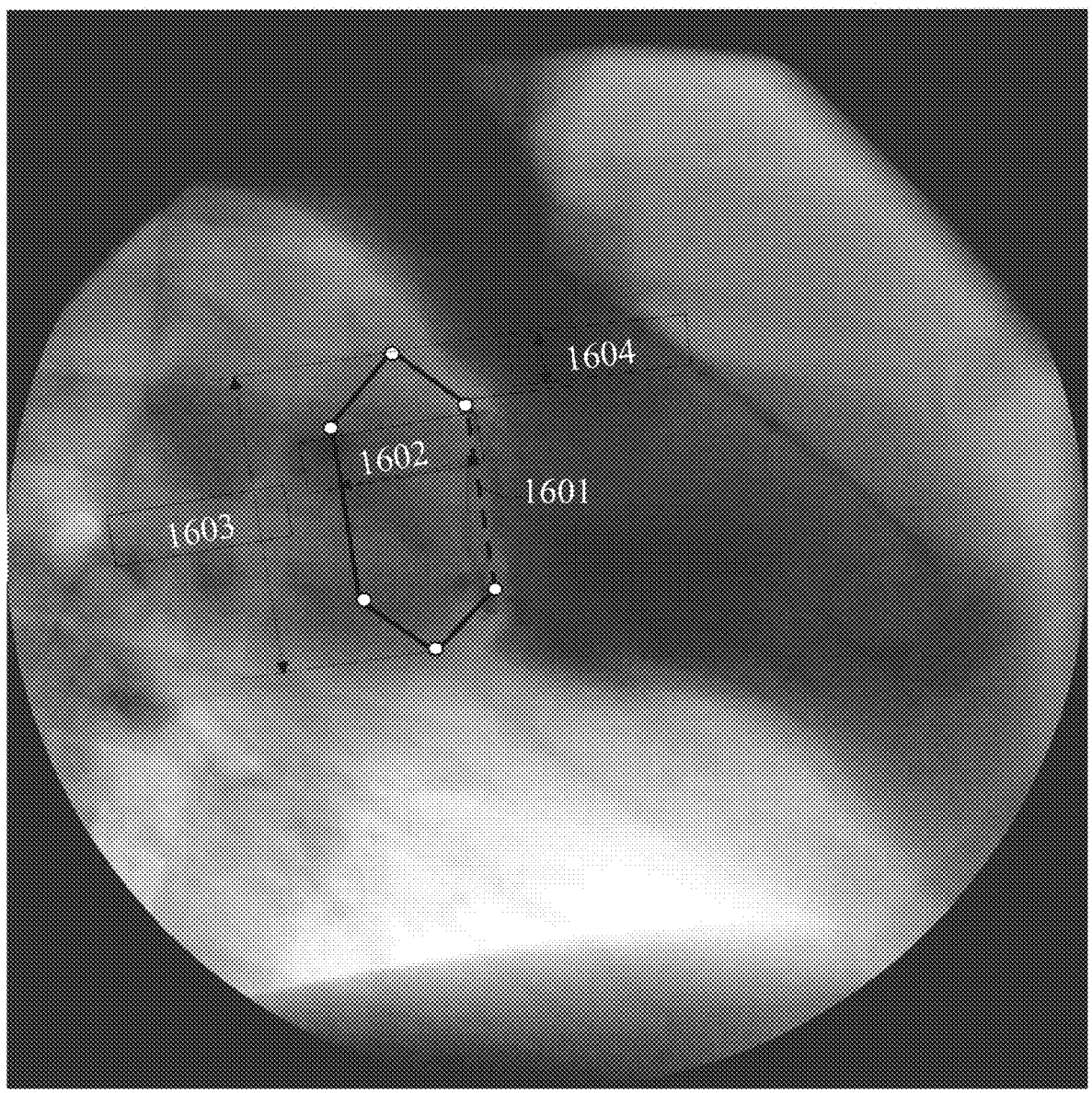
FIG. 16 shows the definition of the LA-region by means of a hexagon shape.

Alternatively, the contour or region of the LA can be a pre-defined shape, such as a hexagon-shape as illustrated by FIG. 16. The hexagon shape is initiated by the drawing of line segment 1601, which result in a hexagon shape with distance 1602, 1603 and 1604 depended on the initial length of 1601. Afterwards, the user can change the size of the shape (1601, 1602, 1603 and 1604) by dragging on the dots. The same principle can be applied when the hexagon shape is initiated by another line segment of the circumference of the hexagon.

Figure 9:
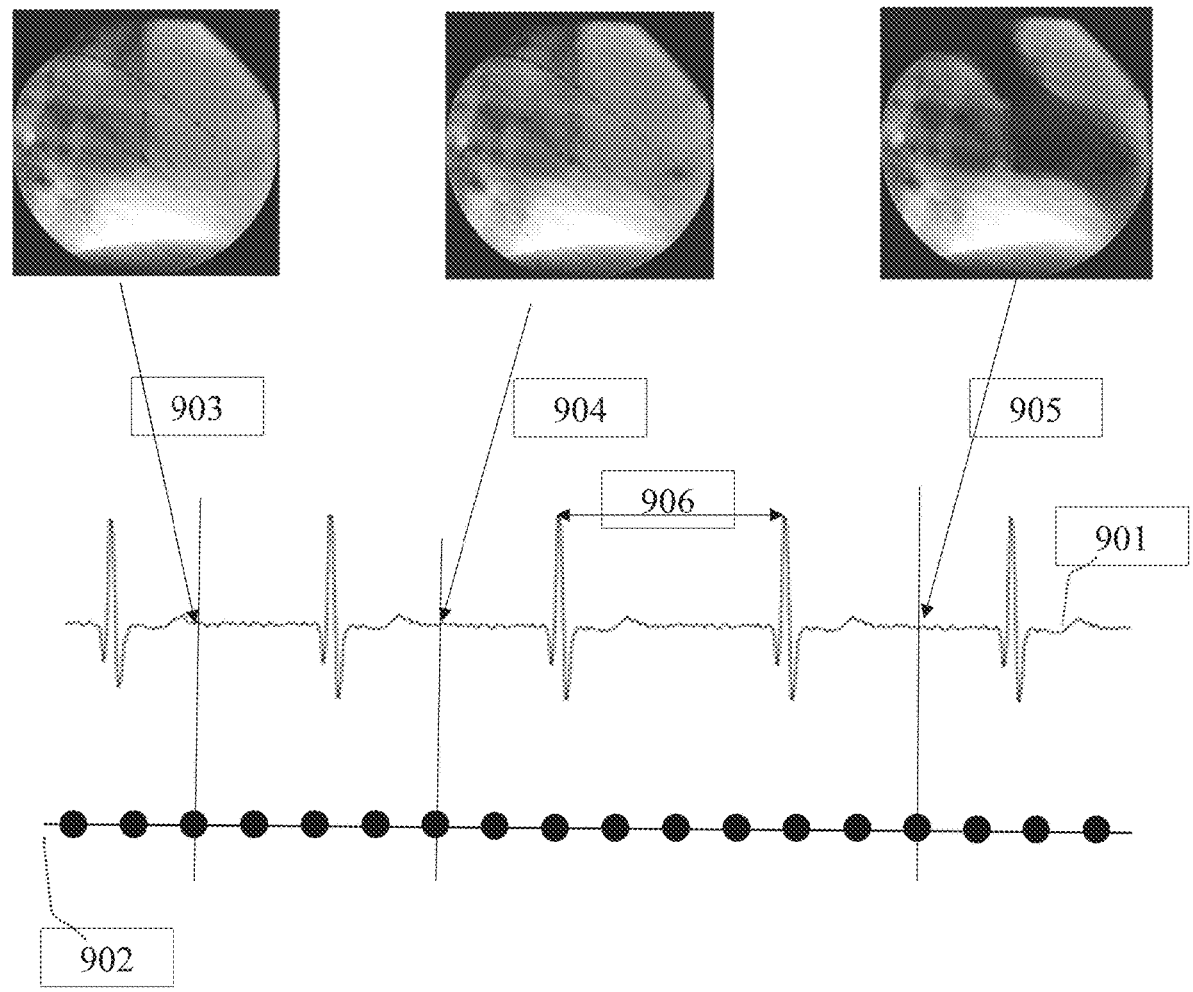
FIG. 9 illustrates the creation of the densitometric image sequence.
Figure 10:
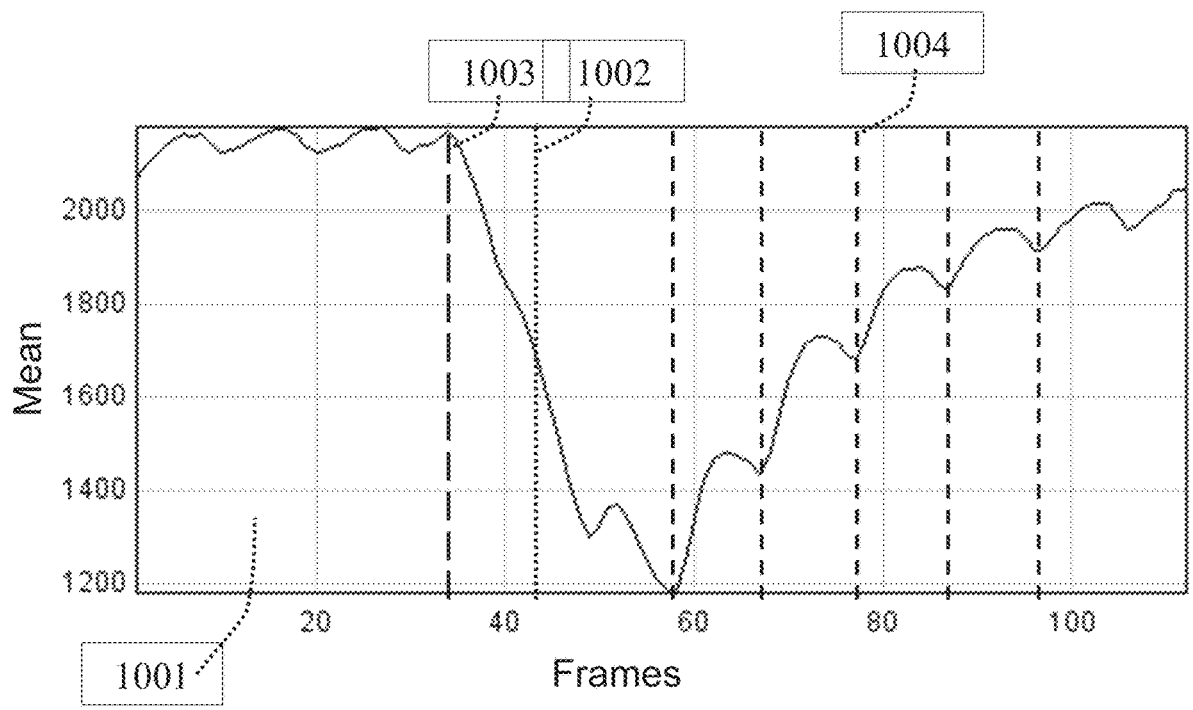
FIG. 10 shows the mean pixel intensity of each frame within the image sequence.

Within step 103 of FIG. 1, the x-ray angiographic sequence obtained in step 101 is converted into a densitometric image sequence. FIG. 9 illustrated the creation of the densitometric image sequence using the ECG signal as available through the "headers" of the DICOM file format. The ECG signal is represented by 901, and the x-ray angiographic image sequence is represented by 902 in which each successive frame is represented by a dot. Picture 903 represent a frame from the sequence in which no contrast liquid is present and picture 905 represents a frame from the sequence in which contrast liquid is present. The frame in which the contrast in the left ventricle arrives (further referred to as $f_c$) is illustrated by 904. This frame can be defined manually or can be automatically detected by analyzing the global intensity distribution of each frame, expressed as for instance the mean intensity, within the acquired x-ray sequence. Before the contrast is injected the global frame image intensity will be different than after the contrast is injected within the sequence. This is illustrated by FIG. 10 which shows the mean pixel intensity of each frame within the image sequence (1001). Frames at the start of the sequence shows relatively high mean pixel intensity, whereas frames after the injection of contrast shows a relative low mean pixel intensity. This due to the lower pixel values when the x-ray radiation is absorbed by the injected contrast liquid. Within picture 1001 of FIG. 10, frame of contrast arrival ($f_c$) is illustrated by 1003, which can be derived by one-dimensional signal processing techniques. For instance, the first derivative can identify the highest signal change which represent position (1002), and the highest second derivative looking to the left of position 1002 identifies the frame of contrast arrival ($f_c$) (1003). In case no ECG signal is present, the frames which represents the end diastolic phase (1004), which will correspond to the r-top of the ECG, can be detected as well. Since the end diastolic phase will is defined as the phase in which the left ventricular volume is the biggest, this can be seen as a small mean pixel intensity drop (1004) after the frame of contrast arrival ($f_c$). These positions can again be identified by means of one-dimensional signal processing techniques. For instance, the local minimum can be identified by looking at the sign of the second derivative where the first derivative is closest to zero. If the second derivate is positive, we are dealing with a local minimum.

Once the frame of contrast arrival ($f_c$) has been identified (904), a set of masker images is created within one cardiac cycle preceding to the frame $f_c$, and each masker image $M_i$ is coupled to the ECG as a percentage of the r-r interval (906). The densitometric sequence is then generated by first determine the percentage of r-r interval of the current frame and subtraction of the corresponding masker image $M_i$, and repeating this process for all frames within the sequence. In case the percentage of r-r interval of the current frame does not match a percentage r-r interval of the masker frames $M_i$, the nearest neighbor masker frames $M_{nn}$ can be selected. Alternatively, a new masker frame $M_{interpolated}$ can be calculated by a weighted interpolation between the closest masker frames. This process generated a sequence of images in which the pixel values represent the amount of x-ray absorbed by the contrast liquid.

In case the ECG signal is not present, the method as described by the explanation of FIG. 10 (1004) can be used to derive the ECG signal.

Alternatively, the densitometric image sequence can be created as disclose by step 3 of FIG. 1 within U.S. Pat. No. 9,576,360.

Figure 11:
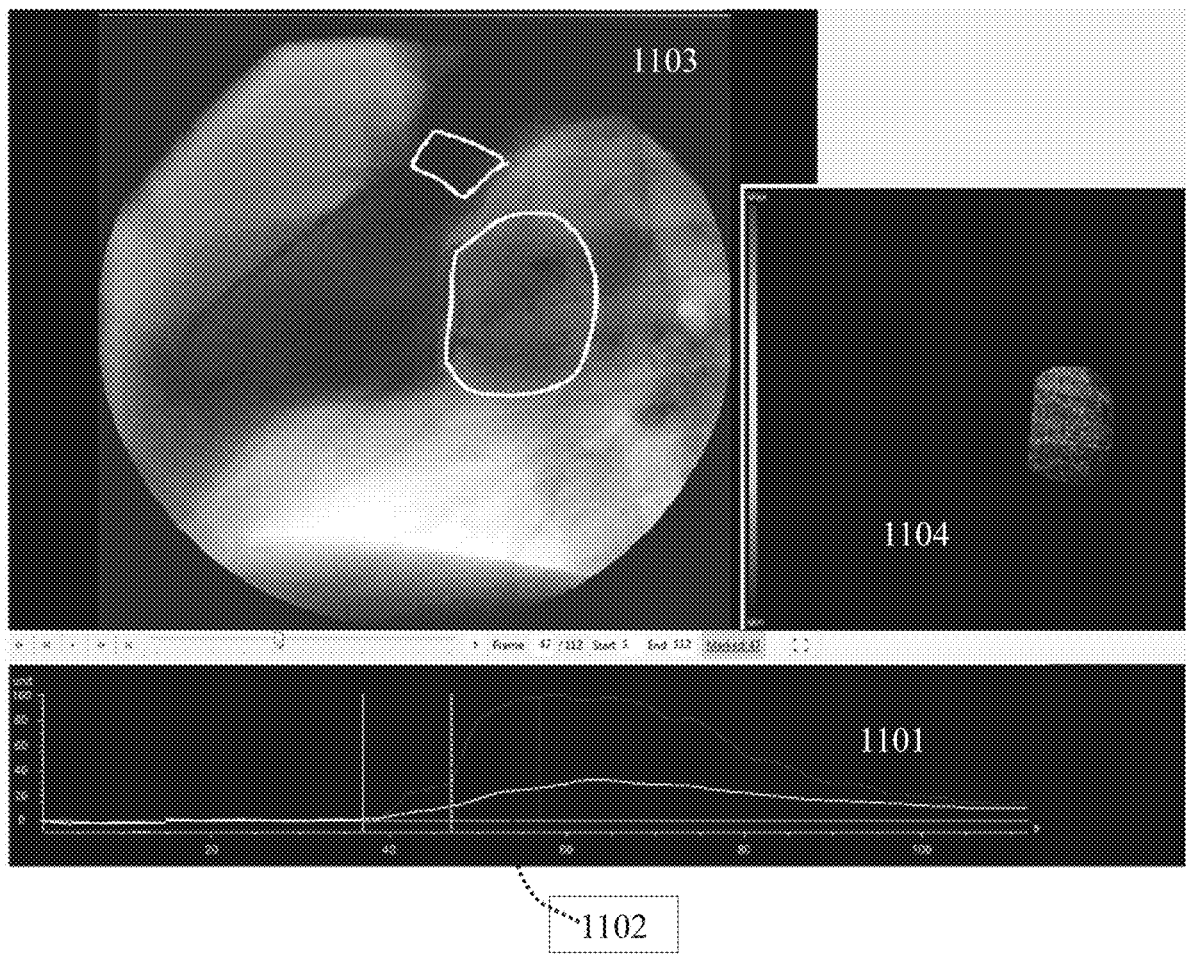
FIG. 11 shown an example of time-density curves.

Within step 104 of FIG. 1, a time-density curve for the contour or region of the AO and a time density curve for the contour or region of the LA are calculated. Such time-density curves represent a time-evolution of pixel brightness of a sequence of images, and in current application the pixel brightness values represent the density of the absorbed x-ray due to the contrast liquid and is computed from the densitometric image sequence. The time-density curve for the contour or region of the AO is computed as the mean pixel intensity within the corresponding region along the entire sequence length and are normalized against the maximum value within the contour or region of the AO. The time-density curve for the contour or region of the LA is computed as the mean pixel intensity within the corresponding region along the entire sequence length, and are normalized against the maximum value within the contour or region of the LA. FIG. 11 shown an example of the time-density curves resulting from the analysis of the image sequence (1103) for the AO region (1101) and the LA region (1102).

Optionally the time-density curve for the contour or region of the LA can be calculated by taking into consideration the region within the LA which becomes opacified after contrast injection. Since mitral regurgitation can result in provides high local velocity jets, it can occur that only a small region within the LA becomes opacified. To increase the accuracy of the time-density curve computed within the LA-region a method is presented which takes above into consideration. This is done by selecting a number of pixels within the contour of the LA for calculation which exceeds a certain threshold value. This threshold is defined based on a fraction of the mean opacification difference before and after contrast arrival derived within the AO region. This fraction is added to the mean opacification of the LA region before contrast arrival to define the threshold that indicates which pixels from the LA region are included, thus excluding pixels below the given threshold from analysis.

Figure 12:
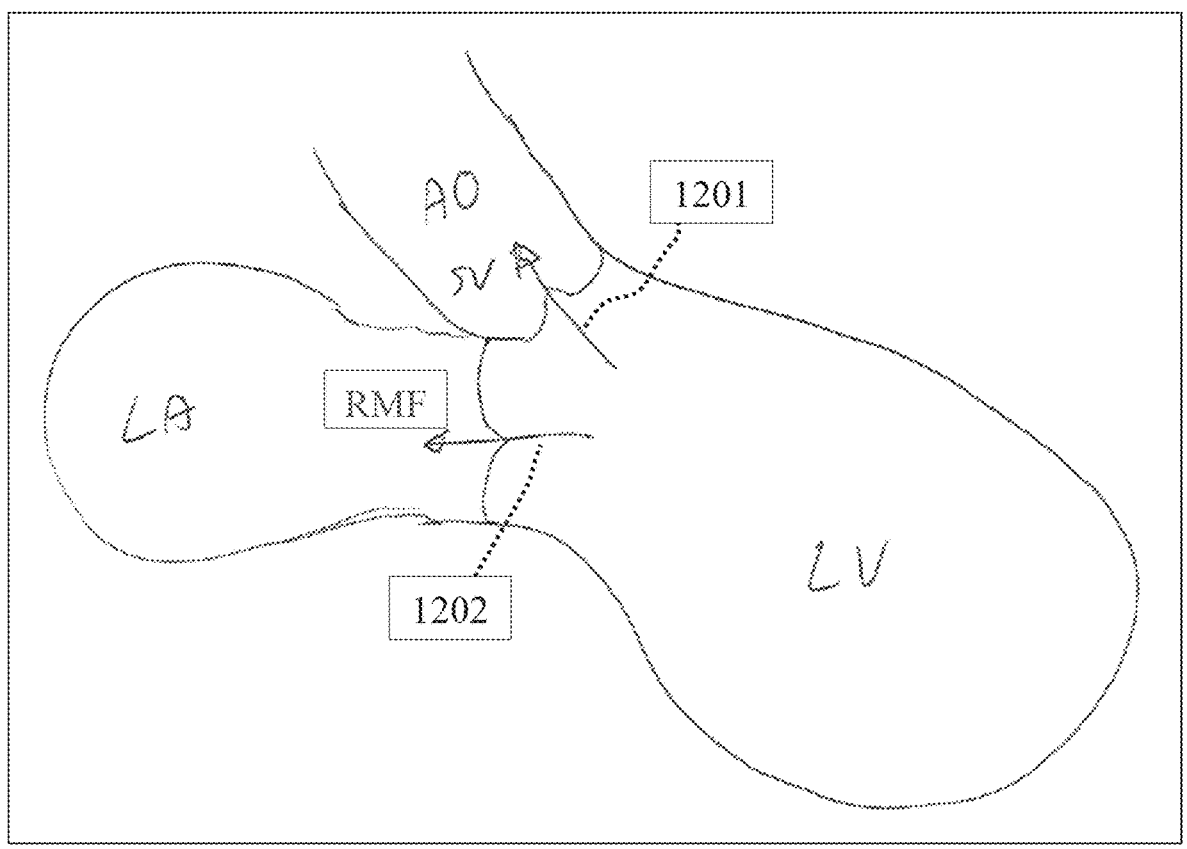
FIG. 12 provides a schematic illustration of mitral regurgitation.

Within step 105 of FIG. 1, data quantifying valvular regurgitation of the mitral valve is calculated. As depicted by FIG. 3B, during systolic the ventricular valves are open (309) and ventricular ejection takes place. When focusing on the left ventricle, during systole the aortic valve is open and an amount of blood volume within the left ventricle is ejected towards the aorta, which is called the stroke volume (SV) and identified by 1201 within FIG. 12. Any flow from the left ventricle towards the LA during the systolic phase (in which the mitral valve should be fully closed), is called regurgitant mitral flow (RMF) or backwards mitral flow as indicated by 1202 in FIG. 12 and is represented by the term Mitral$_{backward\ flow}$ (unit-less value of flow) in equation (1).

Taking into consideration the conservation law of mass, the following equation applies:

$$\text{Mitral}_{forward\ flow} - \text{Mitral}_{backward\ flow} = \text{Aorta}_{forward\ flow} - \text{Aorta}_{backward\ flow}. \quad \text{Eqn. (1)}$$

Within equation 1, aorta$_{forward\ flow}$ is defined as the flow which is ejected from the left ventricle into the ascending aorta during the systole phase in which the aorta valve is open, mitral$_{forward\ flow}$ is defined as the flow from the left atrium towards the left ventricle during diastole phase in which the mitral valve is open, and aorta$_{backward\ flow}$ is the flow from the ascending aorta towards the left ventricle in diastole phase in which the aortic valve is closed (aortic regurgitant flow). The aorta$_{forward\ flow}$ can be derived from the time-density curve of the AO region, and is calculated by the area under such time-density curve starting from the contrast arrival ($f_c$) over a number of cardiac cycles ($N_c$). $N_c$ can be defined by the user and typically this value is 3. The following equation shows how the aorta$_{forward\ flow}$ can be computed. Note that the term cycle in equation (2) defines the number of frames within the R-R interval, either extracted from the ECG signal or by means of the explanation of FIG. 10.

$$\text{Aorta}_{forward\ flow} = \sum_{i=fc}^{i=(fc+Nc+cycle)} Timedensity_{AO_i}. \quad \text{Eqn. (2)}$$

Similarly, the mitral$_{backward\ flow}$ can be derived from the time-density curve of the LA region by:

$$\text{Mitral}_{backward\ flow} = \sum_{i=fc}^{i=(fc+Nc+cycle)} Timedensity_{LA_i}. \quad \text{Eqn. (3)}$$

Since the time-density curves are normalized, as described by step 104, the computed aorta$_{forward\ flow}$ and mitral$_{backward\ flow}$ is expressed as unit-less value representing the flow.

A mitral regurgitation fraction, which is expressed in percentage and quantifies valvular regurgitation of the mitral valve, can be computed by:

$$\text{Mitral Regurgitation fraction} = \frac{\text{Mitral}_{backward\ flow}}{\text{Mitral}_{forward\ flow}}. \quad \text{Eqn. (4)}$$

When assuming that there is no aorta regurgitation, a mitral regurgitation fraction, which is expressed in percentage and quantifies valvular regurgitation of the mitral valve, can be derived by $$\text{Mitral Regurgitation fraction} = \frac{\text{Mitral}_{backward\ flow}}{\text{Aorta}_{forward\ flow} + \text{Mitral}_{backward\ flow}}. \quad \text{Eqn. (5)}$$

As can be seen by equation 5, a method is defined for quantifying atrioventricular valve regurgitation (e.g. mitral valve regurgitation) without the use of a ventricular measurement (e.g. within the left ventricle to assess mitral valve regurgitation). This approach eliminates the shortcoming in quantifying atrioventricular valve regurgitation of the method as described by U.S. Pat. No. 9,576,360, which assume a reference region of the chamber of the valve in which the regurgitant blood originates from (e.g. for mitral regurgitation, the left ventricle). Due to the relatively large region of the ventricle (the reference region), it not likely to obtain homogeneous contrast filling, which hampers time-density curve assessment. Moreover, the contrast density within the ventricle will be variable by nature, this due to the change in ventricle shape and volume as a result of the cardiac cycle.

Figure 13:
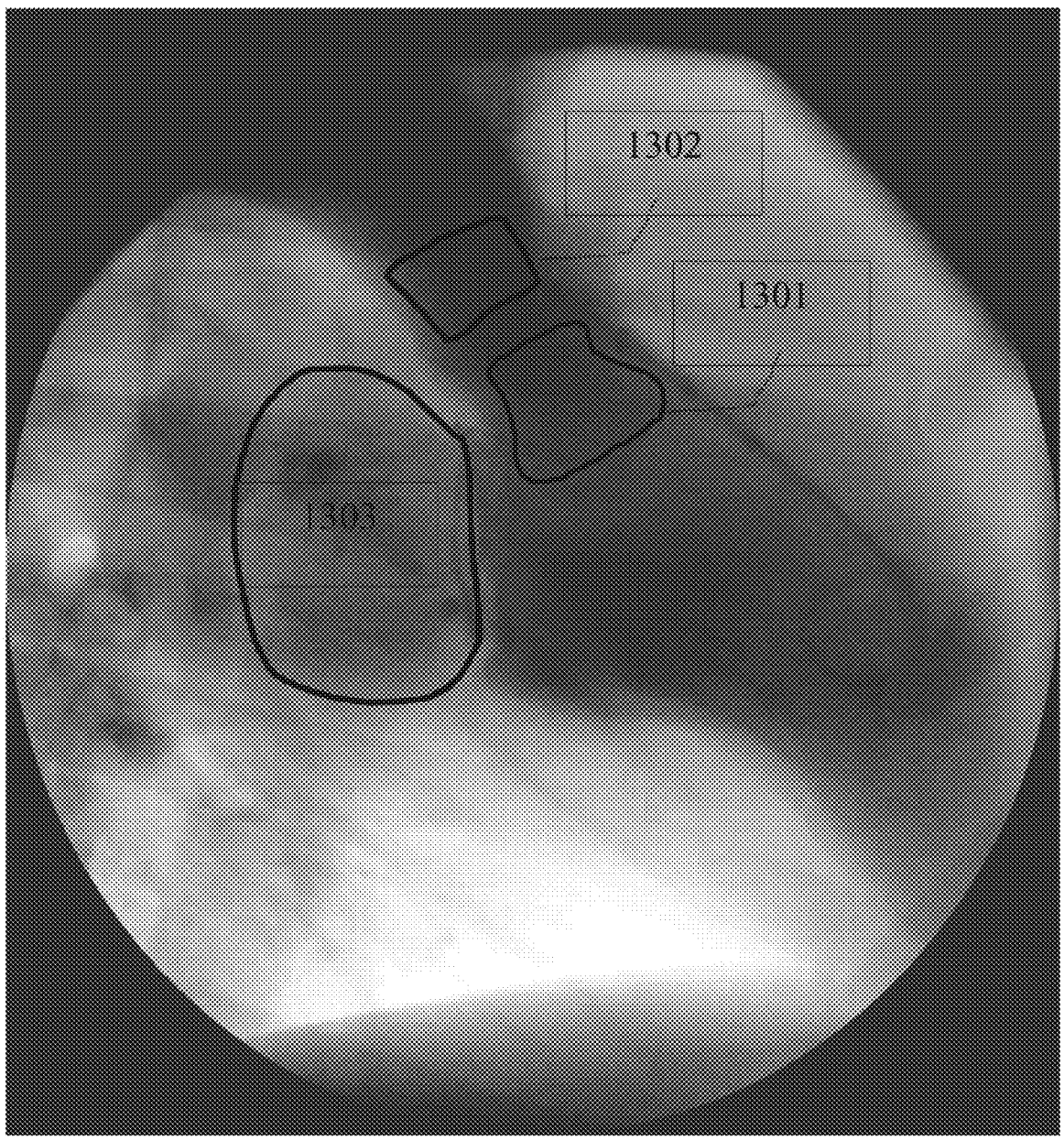
FIG. 13 illustrates an additional object in case aortic regurgitation is present.

Optionally, data quantifying aortic valve regurgitation (which involves aorta$_{backward\ flow}$) can be incorporated into the calculation. For this, an additional region needs to be defined, as illustrated by 1301 within FIG. 13. The additional region (1301) represents the left ventricular outflow track (LVOT), which is further identified as LVOT region. The LVOT region is the part within the left ventricle just below the aortic valve. Within FIG. 13, 1302 represents the AO region and 1303 represents the LA region, similar to FIG. 7. This additional region can be defined by the user or automatically detected by image processing methods for instance as described within this application.

Figure 14:
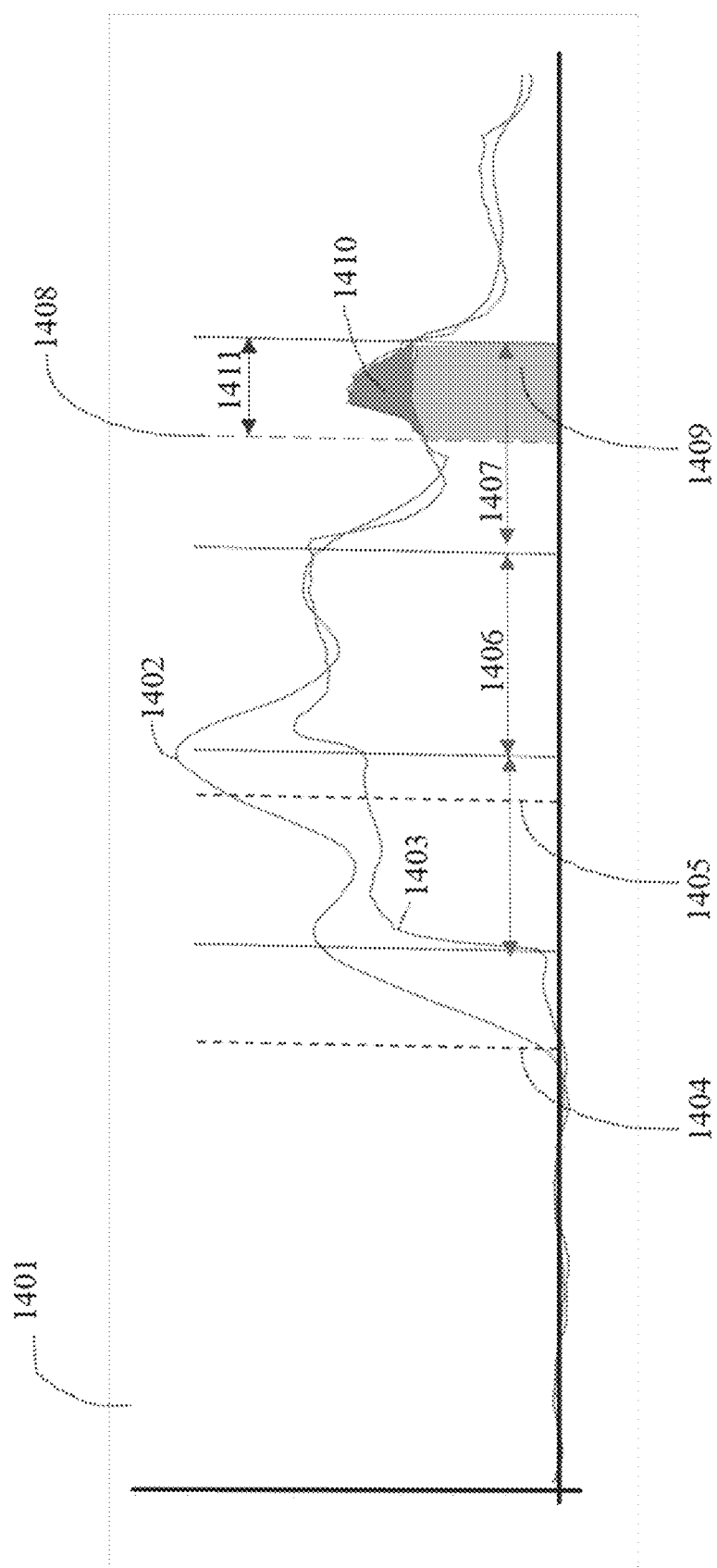
FIG. 14 illustrates the extract the aorta regurgitation from time-density curves.

The extraction of data representing aorta$_{backward\ flow}$ is further illustrated by FIG. 14. Within FIG. 14, 1401 represent the time-density curve of the AO region (1403) and the LVOT region (1402). Note that the time-density normalization is now normalized against the time-density curve with the highest values. In this case the LVOT time-density curve is chosen for normalization. This also means that the time-density curve of the LA region will be normalized against the time-density curve with the highest values and in this particular example this will also be the LVOT time-density curve. The marker depicted by 1404 represents the frame of contrast arrival ($f_c$) and the marker depicted by 1405 represents the frame in which the injection of the contrast liquid stops. The duration of contrast injection is known upfront to the procedure and this frame can be calculated by using the frame rate, duration of contrast injection and $f_c$. The markers between 1406 identifies the R-R interval in frames. Furthermore, for illustration purpose the R-R cycle identified by 1406 shows no aortic regurgitation, as the R-R cycle identified by 1407 shows the behavior of the time-density curve of the AO region and the LVOT region in case aortic regurgitation would be present. From the moment the systolic phase is finalized, in which the aortic valve is closed, the LVOT time-density curve will increase incase aortic regurgitation is present. The aorta$_{backward\ flow}$ can be determined as the area between the LVOT time-density curve and the AO time-density curve within the diastolic phase (1411) and is visualized in FIG. 14 by 1410. Now the mitral regurgitation fraction, which is expressed in percentage and quantifies valvular regurgitation of the mitral valve, can be computed by $$\text{Mitral Regurgitation fraction} = \frac{\text{Mitral}_{backward\ flow}}{\text{Aorta}_{forward\ flow} + \text{Mitral}_{backward\ flow} - \text{Aorta}_{backward\ flow}}. \quad \text{Eqn. (6)}$$

Furthermore, an aorta regurgitation fraction, which is expressed in percentage and quantifies aortic valve regurgitation, can be computed by dividing the area identified by 1410 by the area identified by 1409. The area 1410 can be calculated as the area between the time-density curve for the LVOT region and the time-density curve for the AO region over the diastolic phase 1411. The area 1409 can be calculated as the area under the time-density curve for the AO region over the diastolic phase 1411.

Figure 15:
FIG. 15 shows a cut from a screenshot of the LVA workflow of the CAAS Workstation.

Alternatively, regurgitation of the mitral valve can be quantified by data expressed in absolute values, such as milliliter, instead of a percentage value only. For this the left ventricle needs to be segmented in at least the end systolic frame and the end diastolic frame. Such a segmentation can be performed manually, semi-automatically, or automatic as for instance available in CAAS Workstation 8.2—LVA workflow (Pie Medical Imaging, the Netherlands). FIG. 15 shows a cut from the LVA workflow of the CAAS Workstation. Picture 1501 shows the LV segmented in end diastolic phase and 1502 shows the LV segmented in end systolic phase. Using the Simpson method, the LV volume can be calculated as for instance taught by Ino et al., "*Determination of left ventricular volumes by Simpson's rule in infants and children with congenital heart disease*", British Heart Journal 1989 February; 61(2):182-185. From both the end diastolic LV volume (EDV) and end systolic LV volume (ESV), the stroke volume (SV) can be calculated by:

$$SV \; [\text{ml}] = EDV - ESV. \quad\quad \text{Eqn. (7)}$$

Other left ventricle parameters can then be calculated as well, for instance the left ventricle ejection fraction, cardiac output, as well as region wall motion like the centerline model, radial model, slager model, etc.

Next, regurgitation of the mitral valve can be expressed by data in absolute value, for instance in milliliters, by:

$$\text{Mitral regurgitation [ml]} = SV * \text{Mitral Regurgitation fraction} \quad\quad \text{Eqn. (8)}$$

The same is true for quantifying regurgitation of the aortic valve by means of the equation:

$$\text{Aorta regurgitation [ml]} = SV * \text{Aorta Regurgitation fraction} \quad\quad \text{Eqn. (9)}$$

In FIG. 11, picture 1104 shows an example in which the regurgitation within the left atrium is visualized by means of a 2D color map. This 2D color map is derived by combining the results of the LA time-density curve (1102) with its spatial position related to the left atrium. The regurgitant flow through the mitral valve and/or the aortic valve can, in fact, be visualized by means of a color map obtained by the time intensity curves and/or parameters related to such time intensity curves. This can be achieved, for example, by computing within each pixel within the left atrium, the integral of the time density curve scaled to the maximum value within the AO time-density curve. This way of presenting the outcome of the method of the present invention is very powerful. Within FIG. 11, picture 1104, zero regurgitation as derived within a pixel is represented by the color blue, in which high regurgitation as derived within a pixel is represented by a red color in case the color scaling goes from blue (min value) to red (maximum value). Regurgitation maps can, in fact, be displayed overlaid, for example by varying the opacity, with the input images or with related images, either registered or not, such as those obtained from a different imaging modality, thus providing an immediate overview of insufficiency. Regurgitation maps can be presented statically, for example, as the total integral of the time density curve scaled to the reference or dynamically, for example, by displaying the sub integral of the time density curve related to the frame being viewed. The representation of time-density curves as color maps can obviously be achieved independently from any parameter determination and thus numeric indication of insufficiency according to the present invention.

In other embodiments, one or more machine learning systems or other forms of computer-based artificial intelligence can be trained or otherwise configured to detect one or more objects of interest (e.g., contours of relevant regions of the heart organ) and/or extract data characterizing valvular regurgitation of one or more valves of the heart organ directly from the image sequence. The machine learning system(s) can be embodied by one or more artificial neural networks, decision trees, support vector machines, and/or Bayesian networks. The machine learning system(s) can be trained by supervised learning involving of a set of training data, unsupervised learning, or semi-supervised learning.

The disclosed method is not limited to the left side of the heart and can also be performed for the right side of the heart. For this, the patient specific x-ray image data should visualize the right chamber(s) of the heart, the right ventricle and right atrium. Mirroring the method to the right side of the heart, the following is considered. The mitral valve is replaced by the tricuspid valve, and the aortic valve is replaced by the pulmonary valve. Furthermore, the left atrium is replaced by the right atrium, the left ventricle is replaced by the right ventricle, and the left ventricular outflow track from the left ventricle to the ascending aorta is replaced by the right ventricular outflow track from the right ventricle to the pulmonary artery. The volumes used to calculate the stroke volume of equation 7 represents the ED and ES volume of the right ventricle, as for instance taught by Graham TP et al., "*Right ventricular volume determinations in children, normal values and observations with volume or pressure overload*", Circulation; January 1973, pp 144-153.

Figure 17:
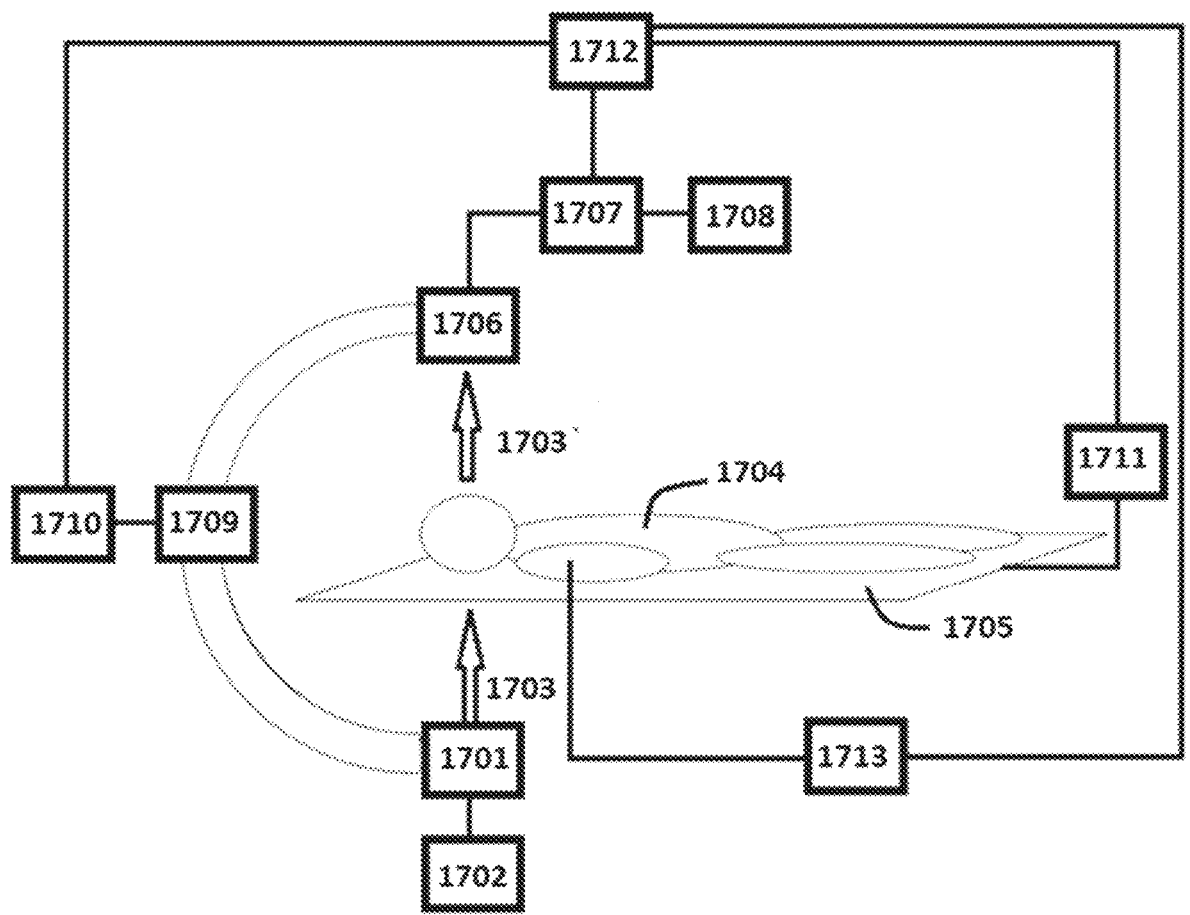
FIG. 17 shows an example of an x-ray cinephotographic unit block diagram in accordance with embodiments herein.

Operations can be performed by processor unit on a standalone system, or a semi-standalone system which is connected to the X-ray cinefluorograpic system (FIG. 2) or any other image system to acquire two-dimensional angiographic image sequences. FIG. 17 illustrates an example of a high-level block diagram of an x-ray cinefluorograpic system. In this block diagram an example is shown on how embodiments could integrate in such a system.

Portions of the system (as defined by various functional blocks) may be implemented with dedicated hardware, analog and/or digital circuitry, and/or one or more processors operating program instructions stored in memory.

The X-ray system of FIG. 17 includes an X-ray tubes 1701 with a high voltage generator 1702 that generates an X-ray beam 1703. The high voltage generator 1702 controls and delivers power to the X-ray tube 1701. The high voltage generator 1702 applies a high voltage across the vacuum gap between the cathode and the rotating anode of the X-ray tube 1701. Due to the voltage applied to the X-ray tube 1701, electron transfer occurs from the cathode to the anode of the X-ray tube 1701 resulting in X-ray photon-generating effect also called Bremsstrahlung. The generated photons form an X-ray beam 1703 directed to the image detector 1706.

An X-ray beam 1703 comprises of photons with a spectrum of energies that range up to a maximum determined by among others the voltage and current submitted to the X-ray tube 1701. The X-ray beam 1703 then passes through the patient 1704 that lies on an adjustable table 1705. The X-ray photons of the X-ray beam 1703 penetrate the tissue of the patient to a varying degree. Different structures in the patient 1704 absorb different fractions of the radiation, modulating the beam intensity. The modulated X-ray beam 1703' that exits from the patient 1704 is detected by the image detector 1706 that is located opposite of the X-ray tube. This image detector 1706 can either be an indirect or a direct detection system.

In case of an indirect detection system, the image detector 1706 comprises of a vacuum tube (the X-ray image intensifier) that converts the X-ray exit beam 1703' into an amplified visible light image. This amplified visible light image is then transmitted to a visible light image receptor such as a digital video camera for image display and recording. This results in a digital image signal.

In case of a direct detection system, the image detector 1706 comprises of a flat panel detector. The flat panel detector directly converts the X-ray exit beam 1703' into a digital image signal. The digital image signal resulting from the image detector 1706 is passed through a digital image processing unit 1707. The digital image processing unit 1707 converts the digital image signal from 1706 into a corrected X-ray image (for instance inverted and/or contrast enhanced) in a standard image file format for instance DICOM. The corrected X-ray image can then be stored on a hard drive 1708.

Furthermore, the X-ray system of FIG. 17 comprises of a C-arm 1709. The C-arm holds the X-ray tube 1701 and the image detector 1706 in such a manner that the patient 1704 and the adjustable table 1705 lie between the X-ray tube 1701 and the image detector 1706. The C-arm can be moved (rotated and angulated) to a desired position to acquire a certain projection in a controlled manner using the C-arm control 1710. The C-arm control allows for manual or automatic input for adjustment of the C-arm in the desired position for the X-ray recording at a certain projection.

The X-ray system of FIG. 17 can either be a single plane or a bi-plane imaging system. In case of a bi-plane imaging system, multiple C-arms 1709 are present each consisting of an X-ray tube 1701, an image detector 1706 and a C-arm control 1710.

Additionally, the adjustable table 1705 can be moved using the table control 1711. The adjustable table 1705 can be moved along the x, y and z axis as well as tilted around a certain point.

Furthermore, a measuring unit 1713 is present in the X-ray system. This measuring unit contains information regarding the patient, for instance information regarding ECG, aortic pressure, biomarkers, and/or height, length etc.

A general unit 1712 is also present in the X-ray system. This general unit 1712 can be used to interact with the C-arm control 1710, the table control 1711, the digital image processing unit 1707, and the measuring unit 1713.

An embodiment is implemented by the X-ray system of FIG. 17 as follows. A clinician or other user acquires at least two X-ray angiographic image sequences of a patient 1704 by using the C-arm control 1710 to move the C-arm 1709 to a desired position relative to the patient 1704. The patient 1704 lies on the adjustable table 1705 that has been moved by the user to a certain position using the table control 1711.

The X-ray image sequences are then generated using the high voltage generator 1702, the X-ray tube 1701, the image detector 1706 and the digital image processing unit 1707 as described above. These images are then stored on the hard drive 1708. Using these X-ray image sequences, the general processing unit 1712 performs the methods as described by present application, as for instance as described by FIG. 1 using the information of the measuring unit 1713, the digital image processing unit 1707, C-arm control unit 1710 and the table control unit 1711.

There have been described and illustrated herein several embodiments of a method and apparatus for restoring missing information regarding the order and the flow direction of the velocity components. While particular embodiments of the invention have been described, it is not intended that the invention be limited thereto, as it is intended that the invention be as broad in scope as the art will allow and that the specification be read likewise. For example, the data processing operations can be performed offline on images stored in digital storage, such as a PACS commonly used in the medical imaging arts. It will therefore be appreciated by those skilled in the art that yet other modifications could be made to the provided invention without deviating from its spirit and scope as claimed.

The embodiments described herein may include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network ("SAN") familiar to those skilled in the art. Similarly, any necessary files for performing the functions attributed to the computers, servers or other network devices may be stored locally and/or remotely, as appropriate. Where a system includes computerized devices, each device can include hardware elements that may be electrically coupled via a bus, the elements including, for example, at least one central processing unit ("CPU" or "processor"), at least one input device (e.g., a mouse, keyboard, controller, touch screen or keypad) and at least one output device (e.g., a display device, printer or speaker). Such a system may also include one or more storage devices, such as disk drives, optical storage devices and solid-state storage devices such as random access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.) and working memory as described above. The computer-readable storage media reader can be connected with, or configured to receive, a computer-readable storage medium, representing remote, local, fixed and/or removable storage devices as well as storage media for temporarily and/or more permanently containing, storing, transmitting and retrieving computer-readable information. The system and various devices also typically will include a number of software applications, modules, services, or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Various embodiments may further include receiving, sending, or storing instructions and/or data implemented in accordance with the foregoing description upon a computer-readable medium. Storage media and computer readable media for containing code, or portions of code, can include any appropriate media known or used in the art, including storage media and communication media, such as, but not limited to, volatile and non-volatile, removable and non-removable media implemented in any method or technology for storage and/or transmission of information such as computer readable instructions, data structures, program modules or other data, including RAM, ROM, Electrically Erasable Programmable Read-Only Memory ("EEPROM"), flash memory or other memory technology, Compact Disc Read-Only Memory ("CD-ROM"), digital versatile disk (DVD) or other optical storage, magnetic cassettes, magnetic tape, magnetic disk storage or other magnetic storage devices or any other medium which can be used to store the desired information and which can be accessed by the system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including" and "containing" are to be construed as open-ended terms (i.e., meaning "including, but not limited to,") unless otherwise noted. The term "connected," when unmodified and referring to physical connections, is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. The use of the term "set" (e.g., "a set of items") or "subset" unless otherwise noted or contradicted by context, is to be construed as a nonempty collection comprising one or more members. Further, unless otherwise noted or contradicted by context, the term "subset" of a corresponding set does not necessarily denote a proper subset of the corresponding set, but the subset and the corresponding set may be equal.

Operations of processes described herein can be performed in any suitable order unless otherwise indicated herein or otherwise clearly contradicted by context. Processes described herein (or variations and/or combinations thereof) may be performed under the control of one or more computer systems configured with executable instructions and may be implemented as code (e.g., executable instructions, one or more computer programs or one or more applications) executing collectively on one or more processors, by hardware or combinations thereof. The code may be stored on a computer-readable storage medium, for example, in the form of a computer program comprising a plurality of instructions executable by one or more processors. The computer-readable storage medium may be non-transitory.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for embodiments of the present disclosure to be practiced otherwise than as specifically described herein. Accordingly, the scope of the present disclosure includes all modifications and equivalents of the subject matter recited in the claims appended hereto as permitted by applicable law. Moreover, any combination of the above-described elements in all possible variations thereof is encompassed by the scope of the present disclosure unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

What is claimed is:

1. A method for characterizing blood flow in an atrioventricular valve of a human heart, the atrioventricular valve connecting an atrium with a corresponding ventricle of the heart, the ventricle being fluidly coupled to a particular vessel that transports blood outside the ventricle, the method comprising:
   a) obtaining two-dimensional (2D) angiographic x-ray image data of the heart, wherein the 2D angiographic x-ray image data covers a first period of time prior to injection of contrast agent into the heart and a second period of time after injection of contrast agent into the heart;
   b) identifying a contour of the atrium within the 2D angiographic x-ray image data of a);
   c) identifying a contour of a region within the particular vessel within the 2D angiographic x-ray image data of a);
   d) converting the 2D angiographic x-ray image data of a) to densitometric image data;
   e) calculating a first time-density curve for the atrium from the contour of the atrium of b) and the densitometric image data of d);
   f) calculating a second time-density curve for the region of the particular vessel from the contour of the region of the vessel of c) and the densitometric image data of d); and
   g) generating data that characterizes at least one regurgitation fraction related to the atrioventricular valve of the heart from the first and second time-density curves of e) and f), respectively, and a contrast arrival frame corresponding to arrival of the contrast agent at the ventricle of the heart in the 2D angiographic x-ray image data;

wherein the data that characterizes at least one regurgitation fraction related to the atrioventricular valve of the heart of g) is derived from second data representing forward blood flow from the ventricle to the particular vessel and first data representing regurgitant blood flow from the ventricle to the atrium;

wherein the second data is calculated by determining area under the second time-density curve of f) starting from the contrast arrival frame over a number of cardiac cycles; and wherein the first data is calculated by determining area under the first time-density curve of e) starting from the contrast arrival frame over the number of cardiac cycles.

2. A method according to claim 1, further comprising
identifying the ventricle of the heart within the 2D angiographic x-ray image data for at least two moments within the cardiac cycle;
calculating a stroke volume based on ventricular volume at the diastolic phase of the heart and ventricular volume at the systolic phase of the heart;
generating data that characterizes regurgitant flow in at least one atrioventricular valve of the heart from the data of g) and the stroke volume.

3. A method according to claim 1, wherein:
the contour of b) corresponds to the left atrium of the heart;
the contour of c) corresponds to a region of the ascending aorta; and
the data of g) characterizes a regurgitation fraction for the mitral valve of the heart.

4. A method according to claim 1, wherein:
the contour of b) corresponds to the right atrium of the heart;
the contour of c) corresponds to a region of the pulmonary artery; and
the data of g) characterizes a regurgitation fraction for the tricuspid valve of the heart.

5. The method of claim 1, wherein:
the densitometric image data of d) comprises pixel values that represent localized density of absorbed radiation due to contrast liquid over time.

6. The method of claim 1, wherein:
the first and second time-density curves of e) and f), respectively, represent localized density of absorbed radiation due to contrast agent by the particular vessel over time.

7. The method of claim 1, wherein:
the contour of c) is identified in a particular image frame.

8. The method of claim 1, wherein:
the contour of c) is identified by user input and/or automatic processes.

9. The method of claim 1, wherein:
at least some of the operations of a) to g) are performed by a processor.

10. The method of claim 1, wherein:
the data of g) is based on conservation of mass of forward and backward flows related to the atrioventricular valve.

11. The method of claim 1, further comprising:
the first and second time density curves of e) and f), respectively, are normalized relative to a selected time density curve.

12. The method of claim 1, wherein:
the data of g) is based on difference between particular time density curves relative to a predefined phase of the heart cycle.

13. The method of claim 1, wherein:
the contrast arrival frame is determined by applying signal processing to the 2D angiographic x-ray image data.

14. A method according to claim 1, further comprising:
calculating a first regurgitant fraction from the second data and the first data.

15. A method according to claim 3, wherein:
the first regurgitant fraction is calculated as $$\frac{AtrioventricularValve_{backward\ flow}}{VentriculaValve_{forward\ flow} + AtrioventrocularValve_{backward\ flow}},$$

wherein $VentriculaValve_{forward\ flow}$ comprises the second data, and $AtrioventricularValve_{backward\ flow}$ comprises the first data.

16. A method according to claim 1, further comprising:
h) identifying a contour of an additional region representing a ventricular outflow track of the heart within the 2D angiographic x-ray image data of a);
i) calculating a third time-density curve for the additional region from the contour of the additional region of h) and the densitometric image data of d); and
j) calculating third data representing regurgitant blood flow from the particular vessel to the ventricle from the third time density curve of i).

17. A method according to claim 16, wherein:
the third data is calculated by determining area between the third time density curve of i) and the second time density curve of f) within the diastolic phase of the heart after the contrast arrival frame.

18. A method according to claim 16, wherein:
the contour of b) corresponds to the left atrium of the heart;
the contour of c) corresponds to a region of the ascending aorta;
the contour of h) corresponds to the left ventricular outflow track of the heart; and
the third data of j) characterizes regurgitant blood flow for the aortic valve of the heart.

19. A method according to claim 16, wherein:
the contour of b) corresponds to the right atrium of the heart;
the contour of c) corresponds to a region of the pulmonary artery;
the contour of h) corresponds to the right ventricular outflow track of the heart; and
the third data of j) characterizes regurgitant blood flow for the pulmonary valve of the heart.

20. A method according to claim 16, further comprising:
calculating a second regurgitant fraction from the third data.

21. A method according to claim 20, wherein:
the second regurgitant fraction is calculated as $$\frac{AtrioventricularValve_{backward\ flow}}{VentricularValve_{forward\ flow} -},$$

$$VentricularValve_{backward\ flow} +$$

$$AtrioventrocularValve_{backward\ flow}$$

wherein VentriculaValve$_{forward\ flow}$ comprises the second data, AtrioventricularValve$_{backward\ flow}$ comprises the first data, and VentricularValve$_{backward\ flow}$ comprises the third data.

22. An imaging system for characterizing blood flow in an atrioventricular valve of a human heart, the atrioventricular valve connecting an atrium with a corresponding ventricle of the heart, the ventricle being fluidly coupled to a particular vessel that transports blood outside the ventricle, the imaging system comprising:
- a data acquisition system configured to acquire two dimensional (2D) angiographic x-ray image data of the heart, wherein the 2D angiographic x-ray image data covers a first period of time prior to injection of contrast agent into the heart and a second period of time after injection of contrast agent into the heart; and
- at least one processor configured to execute program instructions for carrying out method steps comprising:
  - a) obtaining the 2D angiographic x-ray image data of the heart;
  - b) identifying a contour of the atrium within the 2D angiographic x-ray image data of a);
  - c) identifying a contour of a region within the particular vessel within the 2D angiographic x-ray image data of a);
  - d) converting the 2D angiographic x-ray image data of a) to densitometric image data;
  - e) calculating a first time-density curve for the atrium from the contour of the atrium of b) and the densitometric image data of d);
  - f) calculating a second time-density curve for the region of the particular vessel from the contour of the region of the vessel of c) and the densitometric image data of d); and
  - g) generating data that characterizes at least one regurgitation fraction related to the atrioventricular valve of the heart from the first and second time-density curves of e) and f), respectively, and a contrast arrival frame corresponding to arrival of the contrast agent at the ventricle of the heart in the 2D angiographic x-ray image data;
- wherein the data that characterizes at least one regurgitation fraction related to the atrioventricular valve of the heart of g) is derived from second data representing forward blood flow from the ventricle to the particular vessel and first data representing regurgitant blood flow from the ventricle to the atrium;
- wherein the second data is calculated by determining area under the second time-density curve of f) starting from the contrast arrival frame over a number of cardiac cycles; and
- wherein the first data is calculated by determining area under the first time-density curve of e) starting from the contrast arrival frame over the number of cardiac cycle.

* * * * *